US010251783B2

(12) United States Patent
Chernyak

(10) Patent No.: US 10,251,783 B2
(45) Date of Patent: *Apr. 9, 2019

(54) METHODS AND SYSTEMS FOR TRACKING A TORSIONAL ORIENTATION AND POSITION OF AN EYE

(71) Applicant: AMO Manufacturing USA, LLC, Santa Ana, CA (US)

(72) Inventor: Dimitri A. Chernyak, Santa Clara, CA (US)

(73) Assignee: AMO MANUFACTURING USA, LLC, Santa Ana, CA (US)

(*) Notice: Subject to any disclaimer, the term of this patent is extended or adjusted under 35 U.S.C. 154(b) by 59 days.

This patent is subject to a terminal disclaimer.

(21) Appl. No.: 15/430,087

(22) Filed: Feb. 10, 2017

(65) Prior Publication Data
US 2017/0151089 A1 Jun. 1, 2017

Related U.S. Application Data

(60) Continuation of application No. 14/258,854, filed on Apr. 22, 2014, now Pat. No. 9,596,983, which is a
(Continued)

(51) Int. Cl.
A61B 3/12 (2006.01)
A61F 9/008 (2006.01)
(Continued)

(52) U.S. Cl.
CPC ............... *A61F 9/008* (2013.01); *A61B 3/00* (2013.01); *A61B 3/0025* (2013.01);
(Continued)

(58) Field of Classification Search
CPC ....... A61F 9/008; G06T 7/337; G06T 7/0014; A61B 3/0025; A61B 3/1015; A61B 3/113; A61B 3/14; G06F 3/013
(Continued)

(56) References Cited

U.S. PATENT DOCUMENTS 4,365,874 A 12/1982 Milburn et al.
4,540,254 A 9/1985 Humphrey
(Continued)

FOREIGN PATENT DOCUMENTS

DE 10014479 A1 10/2001
EP 456166 A1 11/1991
(Continued)

OTHER PUBLICATIONS

Bara S., et al., "Positioning Tolerances for Phase Plates Compensating Aberrations of the Human Eye," Applied Optics, 2000, vol. 39 (19), pp. 3413-3420.
(Continued)

Primary Examiner — James Greece
(74) Attorney, Agent, or Firm — Johnson & Johnson Surgical Vision, Inc.

(57) ABSTRACT

Methods and systems for tracking a position and torsional orientation of a patient's eye. In one embodiment, the present invention provides methods and software for registering a first image of an eye with a second image of an eye. In another embodiment, the present invention provides methods and software for tracking a torsional movement of the eye. In a particular usage, the present invention tracks the torsional cyclorotation and translational movement of a patient's eye so as to improve the delivery of a laser energy to the patient's cornea.

20 Claims, 23 Drawing Sheets

Related U.S. Application Data division of application No. 12/210,933, filed on Sep. 15, 2008, now Pat. No. 8,740,385, which is a continuation of application No. 11/775,840, filed on Jul. 10, 2007, now Pat. No. 7,431,457, which is a continuation of application No. 11/277,743, filed on Mar. 28, 2006, now Pat. No. 7,261,415, which is a division of application No. 10/300,714, filed on Nov. 19, 2002, now Pat. No. 7,044,602.

(60) Provisional application No. 60/384,653, filed on May 30, 2002.

(51) Int. Cl.
  *A61B 3/10* (2006.01)
  *A61B 3/113* (2006.01)
  *A61B 3/00* (2006.01)
  *G06F 3/01* (2006.01)
  *G06T 7/33* (2017.01)
  *A61B 3/14* (2006.01)
  *G06T 7/00* (2017.01)

(52) U.S. Cl.
  CPC ............ *A61B 3/1015* (2013.01); *A61B 3/113* (2013.01); *A61B 3/14* (2013.01); *A61F 9/00804* (2013.01); *A61F 9/00806* (2013.01); *A61F 9/00829* (2013.01); *G06F 3/013* (2013.01); *G06T 7/0014* (2013.01); *G06T 7/337* (2017.01); *A61F 9/00825* (2013.01); *A61F 2009/0088* (2013.01); *A61F 2009/00844* (2013.01); *A61F 2009/00846* (2013.01); *A61F 2009/00848* (2013.01); *A61F 2009/00872* (2013.01); *A61F 2009/00882* (2013.01); *A61F 2009/00897* (2013.01); *G06T 2207/30041* (2013.01)

(58) Field of Classification Search
  USPC .......................................... 351/205–206, 246
  See application file for complete search history.

(56) References Cited

U.S. PATENT DOCUMENTS

| | | |
|---|---|---|
| 4,641,349 A | 2/1987 | Flom et al. |
| 4,665,913 A | 5/1987 | L'Esperance, Jr. |
| 4,761,071 A | 8/1988 | Baron |
| 4,815,839 A | 3/1989 | Waldorf |
| 4,848,340 A | 7/1989 | Bille et al. |
| 4,932,968 A | 6/1990 | Caldwell et al. |
| 4,995,716 A | 2/1991 | Warnicki et al. |
| 5,036,347 A | 7/1991 | Tsunekawa et al. |
| 5,062,702 A | 11/1991 | Bille |
| 5,070,883 A | 12/1991 | Kasahara |
| 5,098,426 A | 3/1992 | Sklar et al. |
| 5,159,361 A | 10/1992 | Cambier et al. |
| 5,196,873 A | 3/1993 | Yamanobe et al. |
| 5,214,455 A | 5/1993 | Penney et al. |
| 5,231,674 A | 7/1993 | Cleveland et al. |
| 5,291,560 A | 3/1994 | Daugman |
| 5,293,871 A | 3/1994 | Reinstein et al. |
| 5,341,180 A | 8/1994 | Isogai et al. |
| 5,347,331 A | 9/1994 | Isogai et al. |
| 5,398,684 A | 3/1995 | Hardy |
| 5,406,342 A | 4/1995 | Jongsma |
| 5,491,524 A | 2/1996 | Hellmuth et al. |
| 5,512,965 A | 4/1996 | Snook |
| 5,512,966 A | 4/1996 | Snook |
| 5,549,597 A | 8/1996 | Shimmick et al. |
| 5,550,937 A | 8/1996 | Bell et al. |
| 5,572,596 A | 11/1996 | Wildes et al. |
| 5,581,637 A | 12/1996 | Cass et al. |
| 5,614,967 A | 3/1997 | Ishikawa et al. |
| 5,620,436 A | 4/1997 | Lang et al. |
| 5,632,742 A | 5/1997 | Frey et al. |
| 5,640,221 A | 6/1997 | Ishikawa et al. |
| 5,646,791 A | 7/1997 | Glockler |
| 5,649,032 A | 7/1997 | Burt et al. |
| 5,683,379 A | 11/1997 | Hohla |
| 5,713,892 A | 2/1998 | Shimmick |
| 5,740,803 A | 4/1998 | Gray et al. |
| 5,751,836 A | 5/1998 | Wildes et al. |
| 5,757,462 A | 5/1998 | Nanjo |
| 5,774,591 A | 6/1998 | Black et al. |
| 5,777,719 A | 7/1998 | Williams et al. |
| 5,790,235 A | 8/1998 | Kirschbaum |
| 5,843,070 A | 12/1998 | Cambier et al. |
| 5,850,486 A | 12/1998 | Maas, III et al. |
| 5,859,686 A | 1/1999 | Aboutalib et al. |
| 5,865,832 A | 2/1999 | Knopp et al. |
| 5,891,132 A | 4/1999 | Hohla |
| 5,926,251 A | 7/1999 | Okumura |
| 5,951,475 A | 9/1999 | Gueziec et al. |
| 5,963,300 A | 10/1999 | Horwitz |
| 5,974,165 A | 10/1999 | Giger et al. |
| 5,980,513 A | 11/1999 | Frey et al. |
| 5,982,555 A | 11/1999 | Melville et al. |
| 6,004,313 A | 12/1999 | Shimmick et al. |
| 6,095,651 A | 8/2000 | Williams et al. |
| 6,099,522 A | 8/2000 | Knopp et al. |
| 6,104,828 A | 8/2000 | Shioiri |
| 6,116,738 A | 9/2000 | Rorabaugh |
| 6,129,722 A | 10/2000 | Ruiz |
| 6,159,202 A | 12/2000 | Sumiya et al. |
| 6,203,539 B1 | 3/2001 | Shimmick et al. |
| 6,217,596 B1 | 4/2001 | Farah |
| 6,234,631 B1 | 5/2001 | Sarver et al. |
| 6,245,059 B1 | 6/2001 | Clapham |
| 6,257,722 B1 | 7/2001 | Toh |
| 6,266,453 B1 | 7/2001 | Hibbard et al. |
| 6,267,756 B1 | 7/2001 | Feuerstein et al. |
| 6,271,914 B1 | 8/2001 | Frey et al. |
| 6,271,915 B1 | 8/2001 | Frey et al. |
| 6,280,436 B1 | 8/2001 | Freeman et al. |
| 6,285,780 B1 | 9/2001 | Yamakita et al. |
| 6,296,358 B1 | 10/2001 | Cornsweet et al. |
| 6,305,802 B1 | 10/2001 | Roffman et al. |
| 6,314,197 B1 | 11/2001 | Jain et al. |
| 6,347,549 B1 | 2/2002 | Ryan et al. |
| 6,351,573 B1 | 2/2002 | Schneider |
| 6,393,163 B1 | 5/2002 | Burt et al. |
| 6,394,999 B1 | 5/2002 | Williams et al. |
| 6,396,069 B1 | 5/2002 | Macpherson et al. |
| 6,413,251 B1 | 7/2002 | Williams |
| 6,496,594 B1 | 12/2002 | Prokoski |
| 6,500,171 B1 | 12/2002 | Williams et al. |
| 6,508,812 B1 | 1/2003 | Williams et al. |
| 6,612,698 B2 | 9/2003 | Saito et al. |
| 6,634,750 B2 | 10/2003 | Neal et al. |
| 6,634,752 B2 | 10/2003 | Curatu |
| 6,666,857 B2 | 12/2003 | Smith |
| 6,673,062 B2 | 1/2004 | Yee et al. |
| 6,702,806 B2 | 3/2004 | Gray et al. |
| 6,728,424 B1 | 4/2004 | Zhu et al. |
| 6,866,661 B2 | 3/2005 | Gray et al. |
| 6,929,638 B2 | 8/2005 | Gray et al. |
| 7,146,983 B1 * | 12/2006 | Hohla .................... A61B 5/117 128/898 |
| 7,261,415 B2 * | 8/2007 | Chernyak ............ A61B 3/1015 351/209 |
| RE39,882 E | 10/2007 | Mihashi et al. |
| 7,309,126 B2 | 12/2007 | Mihashi et al. |
| 7,431,457 B2 * | 10/2008 | Chernyak ............ A61B 3/1015 351/205 |
| 7,458,683 B2 * | 12/2008 | Chernyak ............ A61B 3/0025 351/205 |
| 2002/0013573 A1 | 1/2002 | Telfair et al. |
| 2002/0047992 A1 | 4/2002 | Graves et al. |
| 2003/0156257 A1 | 8/2003 | Levola |
| 2003/0223037 A1 | 12/2003 | Chernyak |
| 2004/0012760 A1 | 1/2004 | Mihashi et al. |
| 2004/0019346 A1 | 1/2004 | Chernyak |

(56) References Cited

U.S. PATENT DOCUMENTS

| | | | |
|---|---|---|---|
| 2004/0070730 A1 | 4/2004 | Mihashi et al. |
| 2004/0102765 A1 | 5/2004 | Koenig |
| 2004/0116910 A1 | 6/2004 | Markman |
| 2004/0143245 A1 | 7/2004 | Gray et al. |
| 2004/0169817 A1 | 9/2004 | Grotehusmann et al. |
| 2005/0007551 A1 | 1/2005 | Wakil et al. |
| 2005/0107775 A1 | 5/2005 | Huang et al. |

FOREIGN PATENT DOCUMENTS

| | | | |
|---|---|---|---|
| EP | 765648 | A2 | 4/1997 |
| EP | 770370 | A2 | 5/1997 |
| EP | 1153570 | A1 | 11/2001 |
| EP | 1210003 | A2 | 6/2002 |
| EP | 1221890 | A1 | 7/2002 |
| EP | 1332712 | A1 | 8/2003 |
| EP | 1514509 | A2 | 3/2005 |
| WO | 9201417 | A1 | 2/1992 |
| WO | 9316631 | A1 | 9/1993 |
| WO | 9418883 | A1 | 9/1994 |
| WO | 9527453 | A1 | 10/1995 |
| WO | 9611655 | A1 | 4/1996 |
| WO | 9927334 | A1 | 6/1999 |
| WO | 0027273 | A1 | 5/2000 |
| WO | 0111418 | A1 | 2/2001 |
| WO | 0128476 | A1 | 4/2001 |
| WO | 0166029 | A1 | 9/2001 |
| WO | 0178584 | A2 | 10/2001 |
| WO | 0185045 | A1 | 11/2001 |
| WO | 0185075 | A1 | 11/2001 |
| WO | 0232298 | A1 | 4/2002 |
| WO | 0232353 | A2 | 4/2002 |
| WO | 02087442 | A1 | 11/2002 |

OTHER PUBLICATIONS

Bos et al, "Ocular Torsion Quantification with Video Images ," IEEE Transactions on Biomedical Engg, pp. 351-357, 1994, vol. 41 (4).

Chaudhuri et al., "Optimum circular fit to weighted data in multi-dimensional space," Pattern Recognition Letters, pp. 1-6 , 1993, vol. 14.

Chiron Technolas GmbH, Keracor Excimer Laser System, User Manual Version 1.0, Aug. 1996, 61 pages total.

Daugman J.G., et al., "High Confidence Visual Recognition of Persons by a Test of Statistical Independence," IEEE Transactions on Pattern Analysis and Machine Intelligence, 1993, vol. 15 (11), pp. 1148-1161.

Daugman, "Wavelet Demodulation Codes, Statistical Independence, and Pattern Recognition," Institute of Mathematics and Its Applications, pp. 244-260 , 2000.

Fitzgibbon A., et al., "Direct Least Square Fitting of Elipses," IEEE Transactions on Pattern Analysis and Machine Intelligence, 1999, vol. 21 (5), pp. 476-480.

Groen E., et al., Video-Oculography, Chapter 1 PhD Thesis, The Dutch Experiment Support Center [online], 1997 [retrieved on Jul. 20, 2005]. Retrieved from the Internet:.

Groen et al., "Determination of Ocular Torsion by Means of Automation Pattern Recognition," IEEE Trans Biomed, pp. 471-479, 1996, vol. 43 (5).

Guirao A., et al., "Corneal Wave Aberration from Videokeratography: Accuracy And Limitations of the Procedure," Journal of the Optical Society of America, 2000, vol. 17 (6), pp. 955-965.

Guirao A., et al., "Effect of Rotation and Translation on the Expected Benefit of an Ideal Method to Correct the Eye'S Higher-Order Aberrations," Journal of the Optical Society of America, 2001, vol. 18 (5), pp. 1003-1015.

Hatamian M. et al., "Design considerations for a real-time ocular counter-roll instrument," IEEE Trans. Biomed. Eng, pp. 278-288, 1983, vol. 30 (5).

International Search Report for Application No. PCT/US2002/37051, dated Apr. 18, 2003, 1 page.

Iskander D.R., et al., "An Alternative Polynomial Representation of the Wavefront Error Function," Investigative Opthalmalogy and Visual Science, 2002, vol. 43 (12), pp. 1.

Iskander D.R., et al., "Modeling of Corneal Surfaces With Radial Polynomials," IEEE Transactions on Biomedical Engineering, 2002, vol. 49 (4), pp. 320-328.

Kremer et al., "How to Keep Lasik on Axis,, 1 page only." Review of Ophthamology, 1999.

Leventon M.E., "A Registration, Tracking and Visualization System for Image Guided Surgery," Massachusetts Institute of Technology, 1997, 123 Pages.

Liang J., et al. "Aberrations and Retinal Image Quality of the Normal Human Eye," Journal of the Optical Society of America A, 1997, vol. 14 (11), pp. 2873-2883.

Liang J., et al, "Objective Measurement Of Wave Aberrations Of The Human Eye With The Use Of A Hartmann-Shack Wave-Front Sensor," Journal of the Optical Society of America, 1994, vol. 11 (7), pp. 1949-1957.

Lim S., et al., "Efficient Iris Recognition through Improvement of Feature Vector and Classifier," ETRI Journal, 2001, vol. 23 (2), pp. 61-69.

Markham C.H., et al., "Eye Torsion in Space and During Static Tilt Pre and Post Spaceflight," 1996, pp. 89-93.

Mulligan B.J., et al., "Image Processing For Improved Eye-Tracking Accuracy," Behavior Research Methods, Instruments, & Computers , 1997, 29, 54-65.

Ott D., et al., "The Stability of Human Eye Orientation during Visual Fixation," Neuroscience Letters, 1992, vol. 142 (2), pp. 183-186.

Roddier F., et al., "Wavefront Reconstruction Using Iterative Fourier Transforms," Applied Optics, 1991, vol. 30 (11), pp. 1325-1327.

Schweigerling J., et al., "Using Corneal Heights Maps And Polynomial Decomposition To Determine Corneal Aberrations," Search Results Optometry & Vision Science, 1997, vol. 74 (11), pp. 906-916.

Sensomotoric Instruments GMBH, "Opposition Against European Patent No. 1221922B1", filed Jun. 27, 2007, 41 pages.

Shi J., et al., "Good Features to Track," Institute of Electrical and Electronics Engineers, 1994, pp. 593-600.

Stevens J., "Astigmatic Excimer Laser Treatment: Theoretical Effects of Axis Misallgnment," Eur. J. Implant Ref. Surg, 1994, vol. 6.

Supplemental Search Report of EP Application No. 027845015, dated Jul. 30, 2008, 6 pages total.

Supplementary European Search Report of EP Patent Application No. EP02784501, dated Jul. 30, 2008, 4 pages total.

Suzuki et al., "Refractive Surgical Problem, >." J. Cataract Refract Surg, pp. 876-881, 1998, vol. 24 (7).

Suzuki et al., "Using a Reference Point and Videokeratography for Inoperative Identification of Astigmatism Axis," J. Cataract Refract Surg, pp. 1491-1495, 1997, vol. 23 (10).

Swami A.U., et al., "Rotational Malposition During Laser In Situ Keratomileusis," American Journal of Opthalmology, 2002, vol. 133 (4), pp. 561-562.

Taylor N.M., et al., "Determining the Accuracy of an Eye Tracking System for Laser Refractive Surgery," Journal of Refractive Surgery, 2000, vol. 16, pp. S643-S646.

Tjon-Fo-Sang M.J., et al., "Cyclotorsion: A Possible Cause of Residual Astigmatism in Refractive Surgery," Journal of Cataract and Refractive Surgery, 2002, vol. 28 (4), pp. 599-602.

"Tracker-Assisted Photorefractive Keratectomy System (T-PRK®)," Operation Manual, pp. 27 & 43-48, 1997, Autonomous Technologies Corporation.

Uozato H., "Centering Corneal Surgical Procedures," American Journal of Ophthalmology, 1987, vol. 103 (3 pt 1), pp. 264-275.

Van Rijn et al., "Instability of ocular torsion during fixation: cyclovergence is more stable than cycloversion ," Vision Res, pp. 1077-1087, 1994, vol. 34 (8).

"Visx Incorporated,Opposition Against European Patent No. 1 221 922 81 , filed Jun. 26, 2007, 28 pages total,".

"VOG for Windows User Manual," Sensomotoric Instruments GMBH , pp. 280, 1996.

(56) References Cited

OTHER PUBLICATIONS

Yamanobe et al., "Eye Movement Analysis System Using Computerized Image Recognition ," Arch Otolaryngol Head NeckSurg, pp. 338-341, 1990, vol. 116 (3).

Yang et al., "Pupil Location Under Mesopic, Photopic, and Pharmacologically Dilated Conditions, ," Investigative Ophthalmology & Visual Science , pp. 2508-2512, 2002, vol. 43 (7).

* cited by examiner

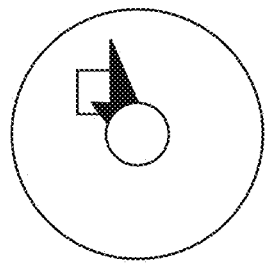 vs 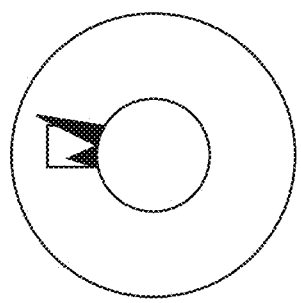
FIG. 7C
 ≠ 
 vs 
FIG. 7D
 = 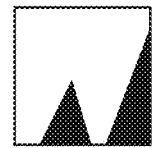

| Eye # | Subject | Eye Color | Eye | Torsion θ | Fit Method | #Points | RMS |
|---|---|---|---|---|---|---|---|
| 1 | AF | Brown | OD | CW 3.1 | sin | 19 | 0.69 |
| 2 | AF | Brown | OS | CW 2.8 | sin | 17 | 0.12 |
| 3 | DC | Blue-gray | OD | CW 4.9 | sin | 13 | 0.60 |
| 4 | DC | Blue-gray | OS | CW 4.8 | sin | 16 | 0.57 |
| 5 | MG | Blue | OD | CW 1.0 | double-sin | 13 | 0.40 |
| 6 | MG | Blue | OS | CW 0.4 | double-sin | 13 | 0.67 |
| 7 | PP | Blue | OD | CCW 6.4 | sin | 12 | 0.31 |
| 8 | PP | Blue | OS | CCW 1.1 | double-sin | 12 | 0.94 |
| 9 | SS | Brown | OD | CCW 3.0 | sin | 13 | 0.20 |
| 10 | SS | Brown | OS | CCW 0.7 | double-sin | 12 | 0.15 |
| 11 | WE | Green | OD1 | CCW 3.3 | sin | 13 | 0.24 |
| 12 | WE | Green | OD2 | CCW 2.8 | sin | 13 | 0.42 |
| 13 | WE | Green | OS | CCW 3.7 | double-sin | 13 | 0.53 |
| 14 | WH | Blue | OD | CW 3.8 | sin | 15 | 0.25 |
| 15 | WH | Blue | OS | CCW 3.7 | sin | 13 | 0.19 |
| 16 | JN | Brown | OS | CW 2.6 | sin | 16 | 0.51 |

FIG. 16A

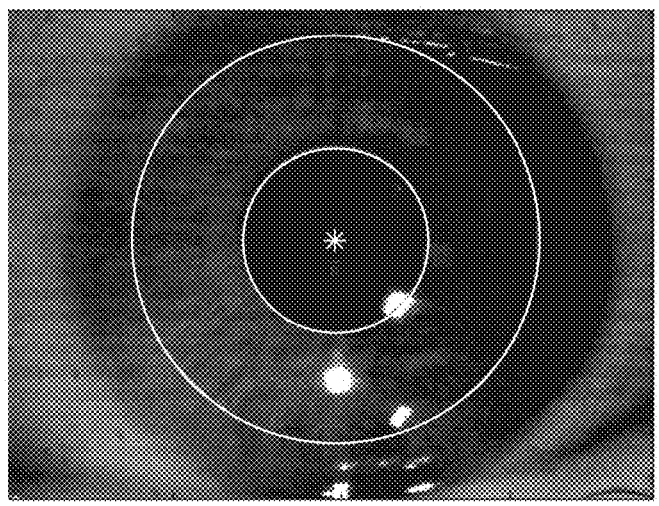

FIG. 17A

| Eye # | Subject | Eye Color | Eye | Torsion θ | Fit Method | #Points | RMS |
|---|---|---|---|---|---|---|---|
| 13 | WE | Green | OS | CCW 2.1 | sin | 13 | 2.04 |

FIG. 17B

| Data | Proc | Angle (M pnts. RMS) | Match Method | Pupil-fit | Success |
|---|---|---|---|---|---|
| 1101_os | PRK | CCW 2.84 (35, 0.92) | LSE | C | yes |
| 1102_od | LASIK | CW 1.49 (19,1.53) | LSE* | E* | yes |
| 1102_os | LASIK | CW 0.20 (21, 1.41) | NXC | E* | yes |
| 1103_od | LASIK | CCW 1.27 (21, 1.39) | LSE* | C | yes |
| 1103_os | LASIK | CW 1.55 (26,1.48) | LSE* | E* | yes |
| 1104_od | LASIK | CCW 7.14 (21, 1.12) | NXC | C | yes |
| 1104_os | LASIK | CW 4.90 (26,1.42) | NXC | C | yes |
| 1105_od | LASIK | CCW 1.29 (20,1.27) | NXC | C | yes |
| 1105_os | LASIK | CW 1.52 (19,1.19) | NXC | C | yes |
| 1106_od | LASIK | CW 5.29(22, 1.42) | NXC | C | yes |
| 1106_os | LASIK | CCW 3.80 (25, 1.12) | NXC | C | yes |
| 1107_od | LASIK | CCW 1.90 (19, 1.15) | NXC | C | yes |
| 1102_os | LASIK | CW 2.79 (18, 0.88) | NXC | C | yes |
| 1108_od | PRK | CCW 0.05 (32, 0.87) | LSE | C | yes |
| 1108_os | PPK | CW 0.29 (27,1.20) | LSE | C | yes |
| 1109_od | LASIK | CW 0.97 (22,1.26) | LSE* | C | yes |
| 1109_os | LASIK | CW 4.53 (29, 0.96) | NXC | C | yes |
| 1110_od | LASIK | CCW 0.66 (21, 1.08) | NXC | C | yes |
| 1110_os | LASIK | CW 0.30 (23,1.44) | NXC | C | yes |
| 1111_od | LASIK | CCW 6.04 (28,1.24) | NXC | C | yes |
| 1111_os | LASIK | CW 8.52 (18, 0.68) | NXC | C | yes |
| 1112_od | LASIK | CCW 6.20 (25,1.02) | NXC | C | yes |
| 1112_os | LASIK | CW 3.83 (19, 1.17) | LSE* | C | yes |
| 1113_od | LASIK | CCW 2.39 (21, 1.18) | NXC | E* | yes |
| 1117_os | LASIK | CCW 2.27 (20,1.04) | NXC | C | yes |
| 1118_od | LASIK | CCW 4.24 (21, 1.34) | NXC | C | yes |
| 1118_os | LASIK | CAW 2.84(21,1.33) | NXC | C | yes |
| 1119_od | LASIK | CCW 5.04 (25,1.57) | NXC | C | yes |
| 1119_os | LASIK | CW 2.29 (24, 0.89) | NXC | C | yes |
| 1120_od | LASIK | CCW 5.05 (25,1.28) | NXC | C | yes |
| 1120_os | LASIK | CW 1.66 (23, 1.43) | NXC | C | yes |
| 1121_od | LASIK | CCW 1.36 (21,1.07) | NXC | C | yes |
| 1121_os | LASIK | CW 3.46 (30,1.23) | NXC | C | yes |
| 1123_od | LASIK | CCW 0.46 (25,1.22) | NXC | C | yes |
| 1123_os | LASIK | CCW 1.78 (26,1.31) | NXC | C | yes |
| 1124_od | LASIK | CW 0.16 (22, 1.00) | NXC | C | yes |
| 1124_os | LASIX | CW 3.42 (27,1.14) | NXC | C | yes |
| 1125_od | LASIK | CCW 1.37 (30, 1.177) | NXC | C | yes |
| 1125_os | LASIK | CW 3.11(28,1.14) | NXC | C | yes |
| 1126_od | LASIK | CCW 1.09 (18, 1.32) | NXC | C | yes |
| 1126_os | LASIK | CW 0.84 (23,1.17) | NXC | C | yes |
| 1127_od | LASIK | CCW 2.26 (27,1.30) | NXC | C | yes |
| 1127_os | LASIK | CW 6.73 (23,1.46) | NXC | C | yes |

FIG. 16B

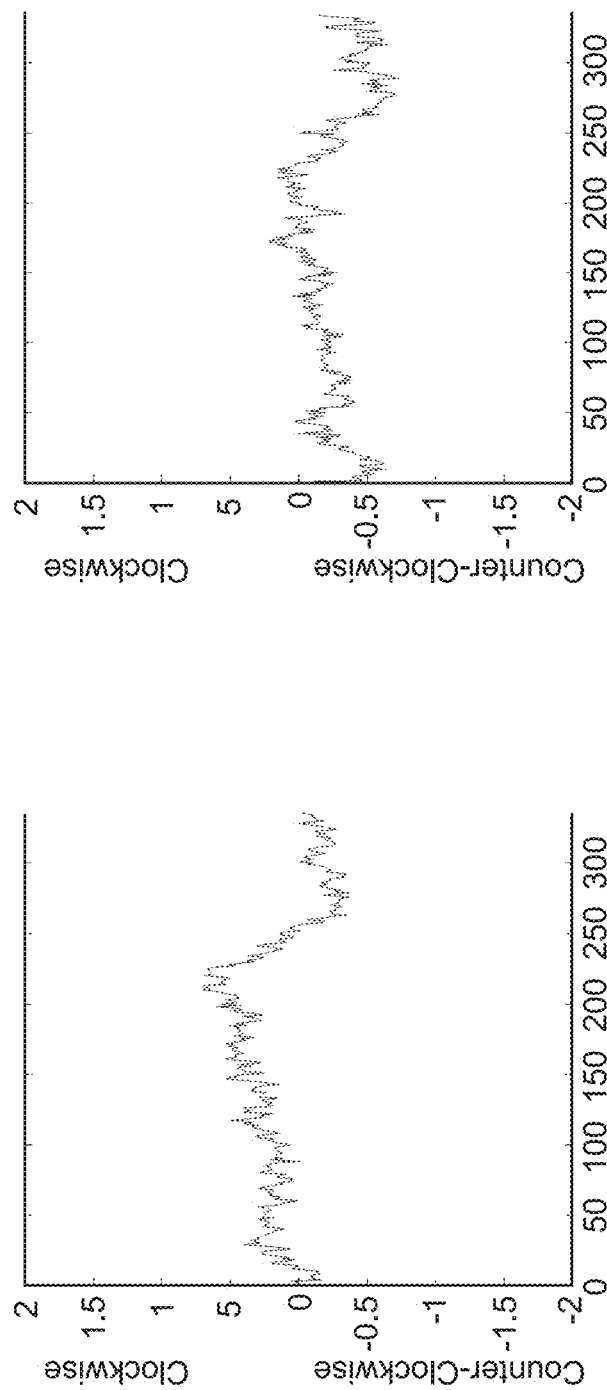

METHODS AND SYSTEMS FOR TRACKING A TORSIONAL ORIENTATION AND POSITION OF AN EYE

CROSS-REFERENCE TO RELATED APPLICATIONS

The present application is a Continuation of U.S. Ser. No. 14/258,854 filed Apr. 22, 2014 (Allowed), which is a Divisional of U.S. Ser. No. 12/210,933 filed Sep. 15, 2008 (now U.S. Pat. No. 8,740,385), which is a Continuation of U.S. Ser. No. 11/775,840 filed on Jul. 10, 2007 (now U.S. Pat. No. 7,431,457); which is a Continuation of U.S. Ser. No. 11/277,743 filed on Mar. 28, 2006 (now U.S. Pat. No. 7,261,415); which is a Divisional of U.S. Ser. No. 10/300,714 filed on Nov. 19, 2002 (now U.S. Pat. No. 7,044,602); which claims the benefit under 35 USC 119(e) of U.S. Provisional Appln. No. 60/384,653 filed on May 30, 2002. The complete disclosures which are incorporated herein by reference in their entirety for all purposes.

BACKGROUND OF THE INVENTION

The present invention relates generally to laser eye surgery methods and systems. More specifically, the present invention relates to registering a first image of a patient's eye with a second image of a patients eye and to tracking a position and a torsional orientation of the patient's eye during laser eye surgery so as to register a customized ablation profile with the patient's eye.

Known laser eye procedures generally employ an ultraviolet or infrared laser to remove a microscopic layer of stromal tissue from the cornea of the eye to alter the refractive characteristics of the eye. The laser removes a selected shape of the corneal tissue, often to correct refractive errors of the eye. Ultraviolet laser ablation results in photo-decomposition of the corneal tissue, but generally does not cause significant thermal damage to adjacent and underlying tissues of the eye. The irradiated molecules are broken into smaller volatile fragments photochemically, directly breaking the intermolecular bonds.

Laser ablation procedures can remove the targeted stroma of the cornea to change the cornea's contour for varying purposes, such as for correcting myopia, hyperopia, astigmatism, and the like. Control over the distribution of ablation energy across the cornea may be provided by a variety of systems and methods, including the use of ablatable masks, fixed and moveable apertures, controlled scanning systems, eye movement tracking mechanisms, and the like. In known systems, the laser beam often comprises a series of discrete pulses of laser light energy, with the total shape and amount of tissue removed being determined by the shape, size, location, and/or number of a pattern of laser energy pulses impinging on the cornea. A variety of algorithms may be used to calculate the pattern of laser pulses used to reshape the cornea so as to correct a refractive error of the eye. Known systems make use of a variety of forms of lasers and/or laser energy to effect the correction, including infrared lasers, ultraviolet lasers, femtosecond lasers, wavelength multiplied solid-state lasers, and the like. Alternative vision correction techniques make use of radial incisions in the cornea, intraocular lenses, removable corneal support structures, thermal shaping, and the like.

Known corneal correction treatment methods have generally been successful in correcting standard vision errors, such as myopia, hyperopia, astigmatism, and the like. However, as with all successes, still further improvements would be desirable. Toward that end, wavefront measurement systems are now available to measure the refractive characteristics of a particular patient's eye. By customizing an ablation pattern based on wavefront measurements, it may be possible to correct minor refractive errors so as to reliably and repeatably provide visual accuities greater than 20/20. Alternatively, it may be desirable to correct aberrations of the eye that reduce visual acuity to less than 20/20. Unfortunately, these measurement systems are not immune from measurement error. Similarly, the calculation of the ablation profile, the transfer of information from the measurement system to the ablation system, and the operation of the ablation system all provide opportunities for the introduction of errors, so that the actual visual accuities provided by real-world wavefront-based correction systems may not be as good as might be theoretically possible.

One potential problem with the use of wavefront measurements is aligning the customized laser ablation pattern with the patient's eye. In order to achieve precise registration between the wavefront measurement and the treatment to be delivered to the patient's eye, the wavefront measurement and the eye should share a common coordinate system. For example, when the wavefront measurement is taken, the patient will generally be in a seated position. However, when the laser eye surgery is being performed, the patient will generally be in a supine position, which may not position the patient's eye in the same position or torsional orientation as the eye when the wavefront measurement was taken.

Moreover, even if the patient is positioned in the same initial position and/or torsional orientation, the eye often undergoes a cyclotorsional rotation. If this rotation is not properly accounted for, the benefits of the refractive surgery would be reduced, particularly in cases of astigmatism and other non-rotationally symmetric aberrations. It has been reported by numerous investigators and researchers that human eyes may undergo torsional movements, usually within 15 degrees from the resting position, but typically it is around 2 to 7 degrees around their axes, during normal activities. The amount of rotation depends on the individual, the stimulus being viewed, and it may depend on the motion and orientation of the person's head and body. Such torsional movement of the patient's eye during the ablation may cause a non-optimal delivery of the customized ablation pattern to the patient's eye, particularly in cases of astigmatism and other-non-rotationally symmetric aberrations.

In light of the above, it would be desirable to provide methods and devices which can accurately register the patient's eye with the customized ablation pattern. Additionally, it would be desirable to account for the positional movement and torsional rotation of the patient's eyes during a laser surgery procedure.

BRIEF SUMMARY OF THE INVENTION

The present invention provides methods and systems which can improve laser eye surgery.

In one aspect, the methods and software of the present invention can register a first image of the patient's eye with a second image of the patient's eye. In some embodiments, the methods can determine a torsional offset $\theta_0$ between the eye in the first image and the eye in the second image.

In one embodiment, a method comprises selecting at least one marker on the iris of the eye in the first image. A corresponding marker is located on the iris in the second image. The first image of the eye and the second image of the eye are registered by substantially matching a common reference point in the first and second images and matching the marker on the iris of the image of the first eye and the marker on the iris of the image of the second eye. Thereafter, a laser treatment can be centered and torsionally aligned with the second image of the eye. In some embodiments, the second image of the eye can be obtained while the patient's eye is aligned with a laser beam that is to deliver the laser treatment.

In some embodiments of the present invention, the common reference point is a pupil center. In other embodiments, the common reference point can be determined through a function of a pupil center and an iris center.

In another embodiment, the first image of the eye is obtained during the measurement of a wavefront (which reflects the lower and higher order optical aberrations in the optical system of the patient's eye) and the second image of the eye is obtained when the patient is positioned in the optical axis of the therapeutic laser. In order to align a laser treatment that is derived from the measured wavefront, the patient's eye in the first image can be registered with the patient's eye when it is positioned in an optical axis of the therapeutic laser so that the laser treatment is delivered in a torsionally correct orientation.

In another aspect, the present invention can track the torsional movement of the eye over time θ(t). Tracking of the torsional orientation of the patient's eye allows a computer processor to adjust a delivery of the customized ablation treatment to account for the changes in the position and orientation of the patient's eye.

In one particular configuration, the present invention provides for torsional tracking of the eye. A tracking algorithm can establish the exact amount of rotation of the eye with respect to the wavefront image taken during the wavefront measurement. This torsional rotation of the eye can be compensated for by making corresponding adjustment of the laser beam delivery.

In one embodiment of a method of the present invention, a reference point (such as a pupil center) is located in a first image of the eye. At least one marker is identified in the first image of the eye. The reference point is also located in a second image of the eye. A corresponding marker is identified in the second image of the eye. A cyclotorsional rotation of the eye is estimated between the first image and second image by comparing the orientation of the at least one markers relative to the pupil center in the first image and the second image.

In another aspect, the present invention provides a method of performing laser eye surgery. The method comprises measuring a wavefront measurement of the patient's eye. An image of the patient's eye is obtained during the measuring of the wavefront measurement. A laser treatment of the patient's eye is generated based on the wavefront measurement. The position of the patient's eye is registered with the image of the patient's eye obtained during the measuring of the wavefront measurement so that the customized laser treatment can accurately delivered to the patient's eye. The laser treatment is delivered to the patient's eye while the torsional orientation of the patient's eye is monitored. The delivery of the laser treatment is adjusted based on the monitored torsional orientation of the patient's eye.

In another aspect, the present invention provide a laser surgery system. In one embodiment, the laser surgery system provides a computer processor configured to receive a first image of an eye and at least one of a wavefront measurement and an ablation pattern for the eye. An eye tracker can be coupled to the computer processor to track a position of the eye under an optical axis of a laser beam. A torsional tracker is coupled to the computer processor to track a torsional orientation of the eye. The computer processor can be configured to adjust a delivery of the ablation pattern based on a change of position and/or torsional orientation of the eye.

In another embodiment, the present invention provides a laser surgery system comprising a system for registering a first image of an eye with a second image of an eye. The system includes a computer processor that is configured to receive a first image of an eye. An imaging device can be coupled to the computer processor. The imaging device can obtain a second image of the eye. The computer processor can be configured to locate a reference point, such as a pupil center, in the first and second image of the eye and locate at least one marker in the first image and find a corresponding marker in the second image. The computer processor can register the first and second image by substantially matching the reference points (e.g., pupil centers) and markers of the first and second image.

For a further understanding of the nature and advantages of the invention, reference should be made to the following description taken in conjunction with the accompanying drawings.

BRIEF DESCRIPTION OF THE DRAWINGS

FIG. 7C illustrates two iris images and texture blocks when the iris ring is not unwrapped;

FIG. 7D illustrates two iris images and texture blocks when the iris ring is unwrapped;

FIGS. 16A and 16B are charts summarizing results for a data set processed by one alignment algorithm of the present invention;

FIG. 17A is an image of an eye that has too much shadow to discern markers;

FIG. 17B is a chart illustrating an eye having an RMS that is above 1;

FIGS. 27A and 27B show measurements of the torsional eye movements with respect to the reference image;

DETAILED DESCRIPTION OF THE INVENTION

The present invention is particularly useful for enhancing the accuracy and efficacy of laser eye surgical procedures such as photorefractive keratectomy (PRK), phototherapeutic keratectomy (PTK), laser in situ keratomileusis (LASIK), and the like. The efficacy of the laser eye surgical procedures can be enhanced by tracking the torsional orientation of the patient's eye so that a laser ablation pattern is more accurately aligned with the real-time orientation of the patient's eye.

While the system and methods of the present invention are described primarily in the context of improving a laser eye surgery system, it should be understood the techniques of the present invention may be adapted for use in alternative eye treatment procedures and systems such as femtosecond lasers and laser treatment, infrared lasers and laser treatments, radial keratotomy (RK), scleral bands, follow up diagnostic procedures, and the like.

Figure 1:
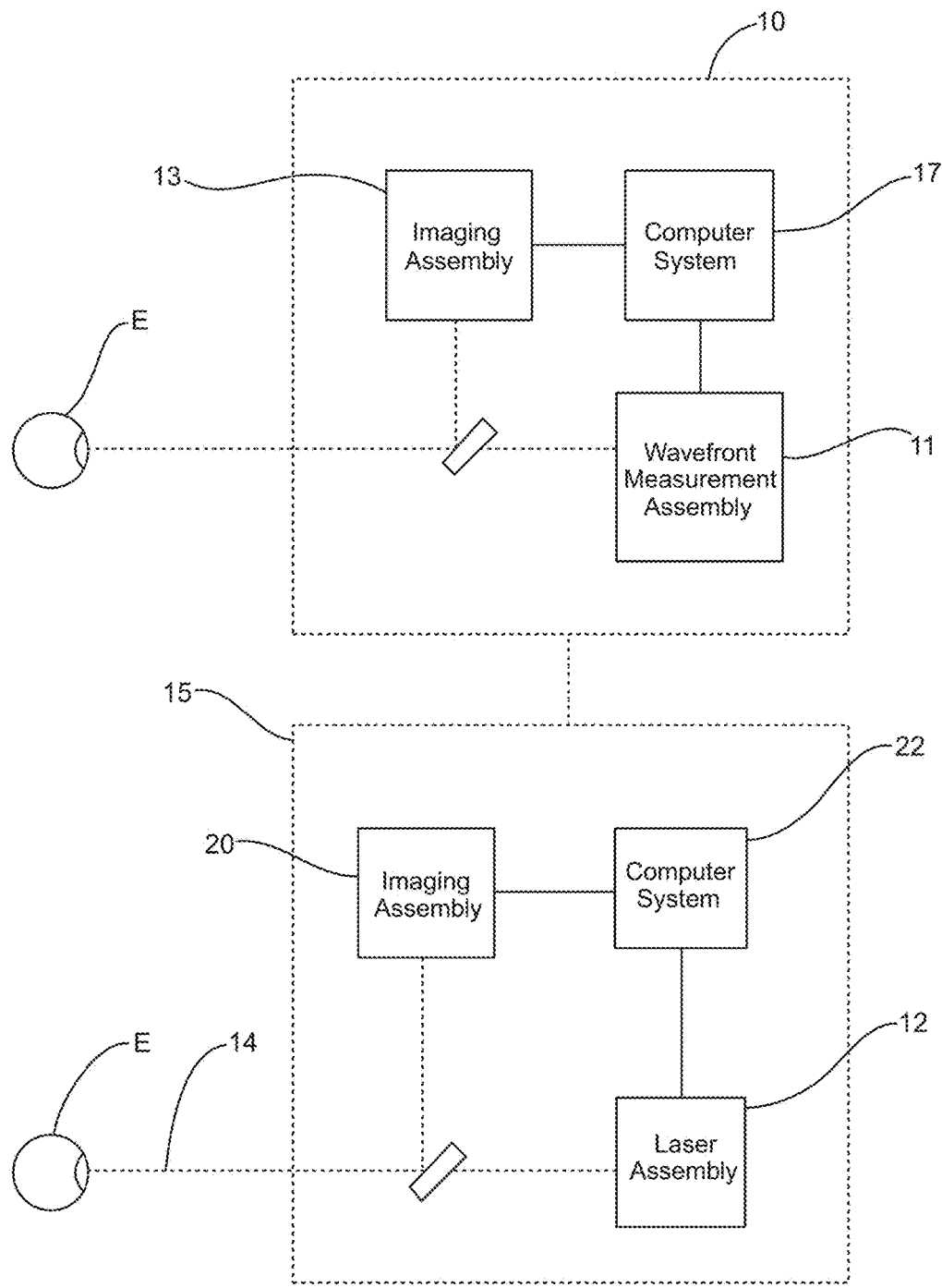
FIG. 1 schematically illustrates a simplified system of the present invention.

FIG. 1 schematically illustrates a simplified system of one embodiment of the present invention. The illustrated system of the present invention can include a laser system 15 coupled to a wavefront measurement device 10 that measures aberrations and other optical characteristics of an entire optical tissue system. The data from such a wavefront measurement device may be used to generate an optical surface from an array of optical gradients. It should be understood that the optical surface need not precisely match an actual tissue surface, as the gradients will show the effects of aberrations which are actually located throughout the ocular tissue system. Nonetheless, corrections imposed on an optical tissue surface so as to correct the aberrations derived from the gradients should correct the optical tissue system. As used herein terms such as "an optical tissue surface" may encompass a theoretical tissue surface (derived, for example, from wavefront sensor data), an actual tissue surface, and/or a tissue surface formed for purposes of treatment (for example, by incising corneal tissues so as to allow a flap of the corneal epithelium to be displaced and expose the underlying stroma during a LASIK procedure).

Figure 2:
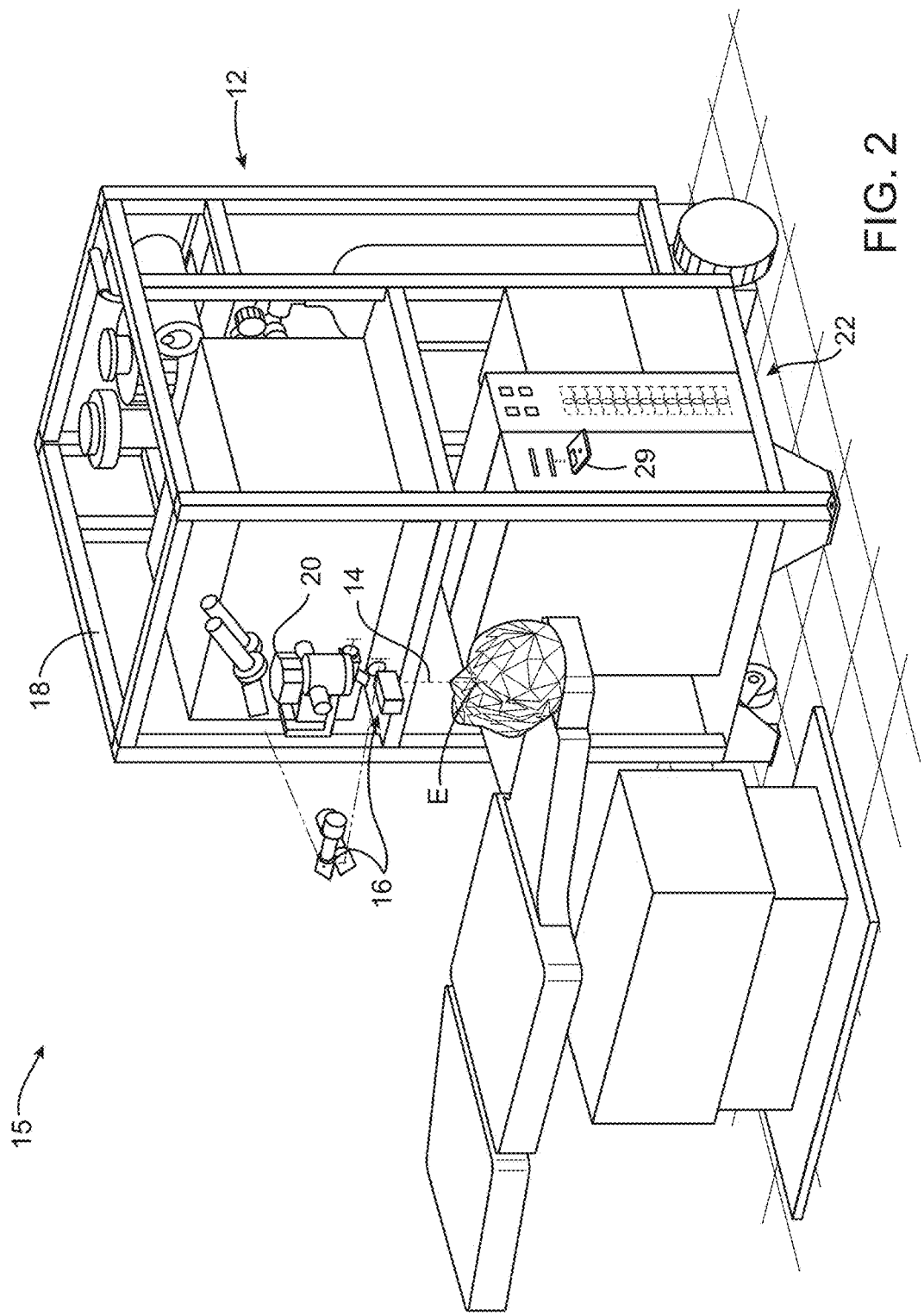
FIG. 2 schematically illustrates one laser surgery system of the present invention.

Referring now to FIGS. 1 and 2, one embodiment of laser eye surgery system 15 of the present invention is illustrated. Laser eye surgery system 15 includes a laser 12 that produces a laser beam 14. Laser 12 is optically coupled to laser delivery optics 16, which directs laser beam 14 to an eye of patient P. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, typically comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention.

Laser 12 and delivery optics 16 will generally direct laser beam 14 to the eye of patient P under the direction of a computer processor 22. Processor 22 will generally selectively adjust laser beam 14 to expose portions of the cornea to the pulses of laser energy so as to effect a predetermined sculpting of the cornea and alter the refractive characteristics of the eye. In many embodiments, both laser 14 and the laser delivery optical system 16 will be under computer control of processor 22 to effect the desired laser sculpting process so as to deliver the customized ablation profile, with the processor ideally altering the ablation procedure in response to inputs from the optical feedback system. The feedback will preferably be input into processor 22 from an automated image analysis system, or may be manually input into the processor by a system operator using an input device in response to a visual inspection of analysis images provided by the optical feedback system. Processor 22 will often continue and/or terminate a sculpting treatment in response to the feedback, and may optionally also modify the planned sculpting based at least in part on the feedback.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. No. 5,683,379, and as also described in co-pending U.S. patent application Ser. No. 08/968,380, filed Nov. 12, 1997; and Ser. No. 09/274,999 filed Mar. 22, 1999, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913 (the full disclosure of which is incorporated herein by reference) and as demonstrated by other scanning laser systems such as the LSX laser by LaserSight, LadarVision by Alcon/Autonomous, and the 217C by Technolas; using masks in the optical path of laser beam 14 which ablate to vary the profile of the beam incident on the cornea, as described in U.S. patent application Ser. No. 08/468,898, filed Jun. 6, 1995 (the full disclosure of which is incorporated herein by reference); hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 15, as should be understood by those of skill in the art. For example, spatial and/or temporal integrators may be included to control the distribution of energy within the laser beam, as described in U.S. Pat. No. 5,646,791, the disclosure of which is incorporated herein by reference. An ablation effluent evacuator/filter, and other ancillary components of the laser surgery system which are not necessary to an understanding of the invention, need not be described in detail for an understanding of the present invention.

As mentioned above, laser system 15 will generally include a computer system or programmable processor 22. Processor 22 may comprise (or interface with) a conventional PC system including the standard user interface devices such as a keyboard, a display monitor, and the like. Processor 22 will typically include an input device such as a magnetic or optical disk drive, a CD drive, an internet connection, or the like. Such input devices will often be used to download a computer executable code from a computer network or a tangible storage media 29 embodying steps or programming instructions for any of the methods of the present invention. Tangible storage media 29 includes, but is not limited to a CD-R, a CD-RW, DVD, a floppy disk, an optical disk, a data tape, a non-volatile memory, or the like, and the processor 22 will include the memory boards and other standard components of modern computer systems for storing and executing this code.

Wavefront measurement device 10 typically includes a wavefront measurement assembly 11 and an imaging assembly 13. Wavefront measurement assembly 11 can be used to measure and obtain a wavefront elevation surface of at least one of the patient's eyes and imaging assembly 13 can obtain still or moving images of the patient's eye during the wavefront measurement.

In exemplary embodiments, imaging assembly 13 is a CCD camera that can obtain a still image of the patient's eye. The image(s) obtained by imaging assembly 13 can thereafter be used to register the wavefront measurement and/or a customized ablation pattern (based on the wavefront measurement) with the patient's eye during the laser surgical procedure.

The wavefront measurement assembly 11 and imaging assembly 13 can be coupled to or integral with a computer system 17 that can generate and store the wavefront measurements and images of the patient's eye. Thereafter, the patient's wavefront data can be stored on a computer readable medium, such as a CD-R, CD-RW, DVD-R, floppy disk, optical disk, a hard drive, or other computer readable medium. Optionally, in some embodiments, the computer system of the wavefront measurement device can generate and save an ablation profile based on the wavefront data.

The wavefront data and/or the customized ablation profile can be loaded into a laser surgical system 15 through reading of the computer readable medium or through delivery into a memory of surgical system 15 over a local or wide-area network (LAN or WAN). Laser eye surgery system 15 can include a computer controller system 22 that is in communication with an imaging assembly 20 and a laser assembly 12. Computer system 22 can have software stored in a memory and hardware that can be used to control the delivery of the ablative energy to the patient's eye, the tracking of the position (translations in the x, y, and z directions and torsional rotations) of the patient's eye relative to an optical axis of laser beam 14, and the like. In exemplary embodiments, among other functions, computer system 22 can be programmed to calculate a customized ablation profile based on the wavefront data, register the image(s) taken with imaging assembly 11 with the image(s) taken by imaging assembly 20, and measure the torsional offset, $\theta_0$, between the patient's eye in the two images. Additionally, computer system 22 can be programmed to measure, in real-time, the movement (x(t), y(t), z(t), and rotational orientation $\theta(t)$) of the patient's eye relative to the optical axis of the laser beam so as to allow the computer system to modify the delivery of the customized ablation profile based on the real-time position of the patient's eye.

Figure 3:
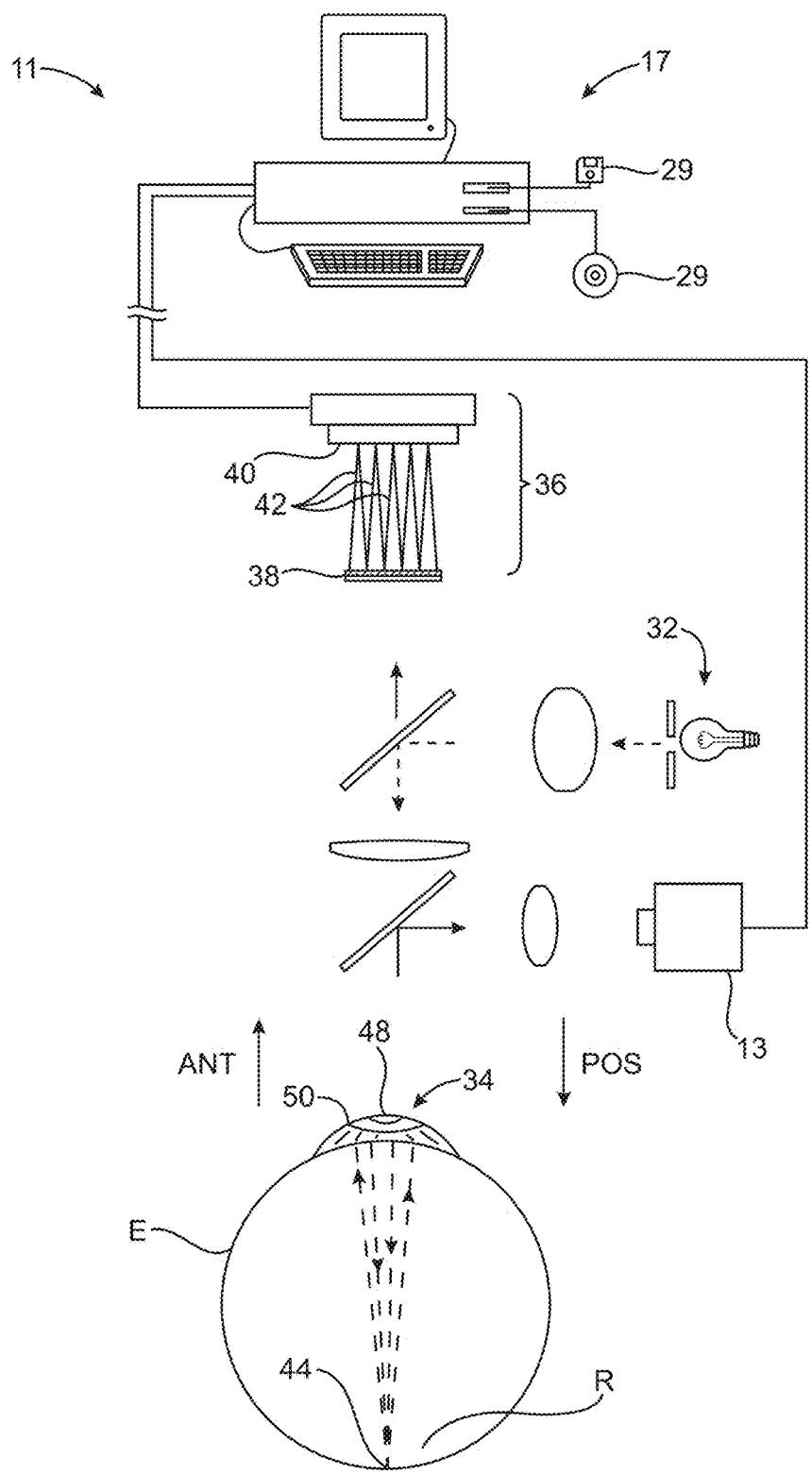
FIG. 3 illustrates one exemplary wavefront measurement device of the present invention.

Referring now to FIG. 3, one embodiment of a wavefront measurement device 10 of the present invention is schematically illustrated. As can be appreciated, the illustrated wavefront measurement device 10 is merely an example of one wavefront measurement device that can be used with the embodiments of the present invention and other conventional or proprietary wavefront measurement devices can be used.

In very general terms, wavefront measurement device 10 includes an imaging assembly 13 that can image the patient's eye E during the wavefront measurement. Wavefront measurement assembly 13 includes an image source 32 which projects a source image through optical tissues 34 of eye E and so as to form an image 44 upon a surface of retina R. The image from retina R is transmitted by the optical system of the eye (specifically, optical tissues 34) and imaged onto a wavefront sensor 36 by system optics 38. The imaging assembly 11 can be in communication with a computer system 22 to deliver the image(s) of the patient's eye to a memory in the computer. Wavefront sensor 36 can also communicate signals to computer 17 for determination of a corneal ablation treatment program. Computer 17 may be the same computer which is used to direct operation of the laser surgery system 15, or at least some or all of the computer components of the wavefront measurement device 10 and laser surgery system may be separate. Data from wavefront sensor 36 may be transmitted to laser system computer 22 via tangible media 29, via an I/O port, via an networking connection such as an intranet, the Internet, or the like.

Wavefront sensor 36 generally comprises a lenslet array 38 and an image sensor 40. As the image from retina R is transmitted through optical tissues 34 and imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or CCD, and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics may decrease lower order optical errors by compensating for spherical and/or cylindrical errors of optical tissues 34. Higher order optical errors of the optical tissues may also be compensated through the use of an adaptive optic element, such as a deformable mirror. Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have well-defined and accurately formed image 44 on retina R.

While the method of the present invention will generally be described with reference to sensing of an image 44 on the retina, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront device 13 by focusing on a fixation target, as described in U.S. Pat. No. 6,004,313, the full disclosure of which is incorporated herein by reference. By varying a focal position of the fixation target as described in that reference, optical characteristics of the eye may be determined while the eye accommodate or adapts to image a field of view at a varying distance. Further alternatives include rotating of the eye by providing alternative and/or moving fixation targets within wavefront device 11.

The location of the optical axis of the eye may be verified by reference to the data provided from an imaging assembly or pupil camera 13 that images the eye concurrently during the wavefront measurements. In the exemplary embodiment, a pupil camera 13 images pupil 50 and/or the iris so as to allow subsequent determination of a position and torsional orientation of the pupil and/or iris for registration of the wavefront sensor data relative to the optical tissues, as will also be described hereinbelow.

Figure 3A:
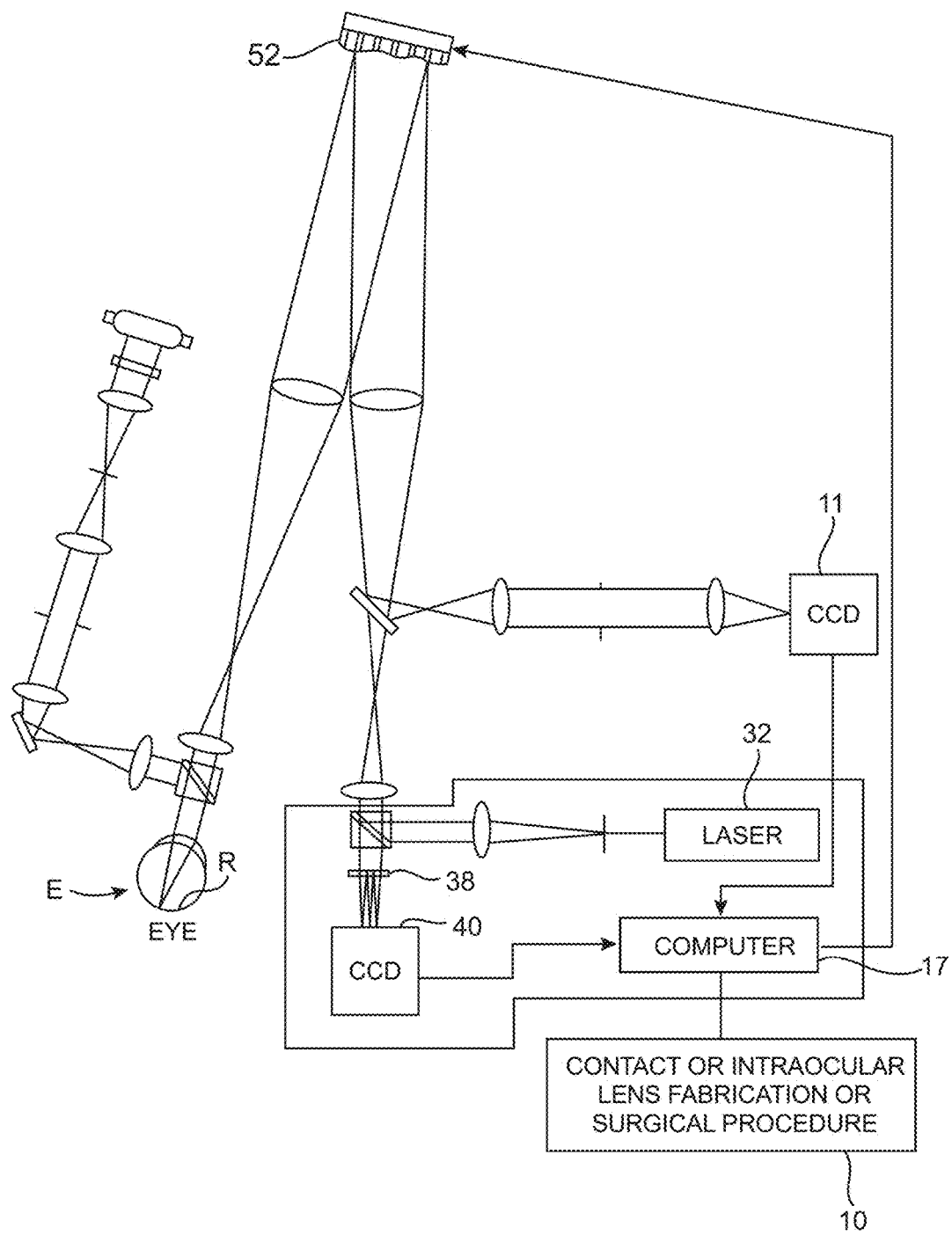
FIG. 3A illustrates an alternative wavefront measurement device of the present invention.

An alternative embodiment of a wavefront sensor system is illustrated in FIG. 3A. The major components of the system of FIG. 3A are similar to those of FIG. 3. Additionally, FIG. 3A includes an adaptive optical element 52 in the form of a deformable mirror. The source image is reflected from deformable mirror 52 during transmission to retina R, and the deformable mirror is also along the optical path used to form the transmitted image between retina R and imaging sensor 40. Deformable mirror 52 can be controllably deformed to limit distortion of the image formed on the retina, and may enhance the accuracy of the wavefront data. The structure and use of the system of FIG. 3A are more fully described in U.S. Pat. No. 6,095,651, the full disclosure of which his incorporated herein by reference.

The components of one embodiment of a wavefront system for measuring the eye and ablations comprise elements of a VISX WaveScan™, available from VISX, Inc. of Santa Clara, Calif. A preferred embodiment includes a WaveScan with a deformable mirror as described above. An alternate embodiment of a wavefront measuring device is described in U.S. Pat. No. 6,271,915, the full disclosure of which is incorporated herein by reference.

A treatment program map may be calculated from the wavefront elevation map so as to remove the regular (spherical and/or cylindrical) and irregular errors of the optical tissues. By combining the treatment program with a laser ablation pulse characteristics of a particular laser system, a table of ablation pulse locations, sizes, shapes, and/or numbers can be developed. An exemplary method and system for preparing such an ablation table is described in co-pending U.S. patent application Ser. No. 09/805,737 filed on Mar. 13, 2001 and entitled "Generating Scanning Spot Locations for Laser Eye Surgery," the full disclosure of which is incorporated herein by reference. Ablation table may optionally be optimized by sorting of the individual pulses so as to avoid localized heating, minimize irregular ablations if the treatment program is interrupted, and the like.

Based on the wavefront measurements of the eye, a corneal ablation pattern may be calculated by processor 17 or 22 (or by another separate processor) for ablating the eye with laser ablation system 15 so as to correct the optical errors of the eye. Such calculations will often be based on both the measured optical properties of the eye and on the characteristics of the corneal tissue targeted for ablation (such as the ablation rate, the refractive index, the propensity of the tissue to form "central islands" or decreased central ablation depths within a uniform energy beam, and the like). The results of the calculation will often comprise an ablation pattern in the form of an ablation table listing ablation locations, numbers of pulses, ablation sizes, and or ablation shapes to effect the desired refractive correction. An exemplary method for generating ablation patterns is described in co-pending U.S. patent application Ser. No. 09/805,737, the full disclosure of which was previously incorporated herein by reference. Where the refractive error is to be corrected by alternative treatment modalities, alternative treatment plans may be prepared, such as corneal ring implant sizes, or the like.

Figure 4:
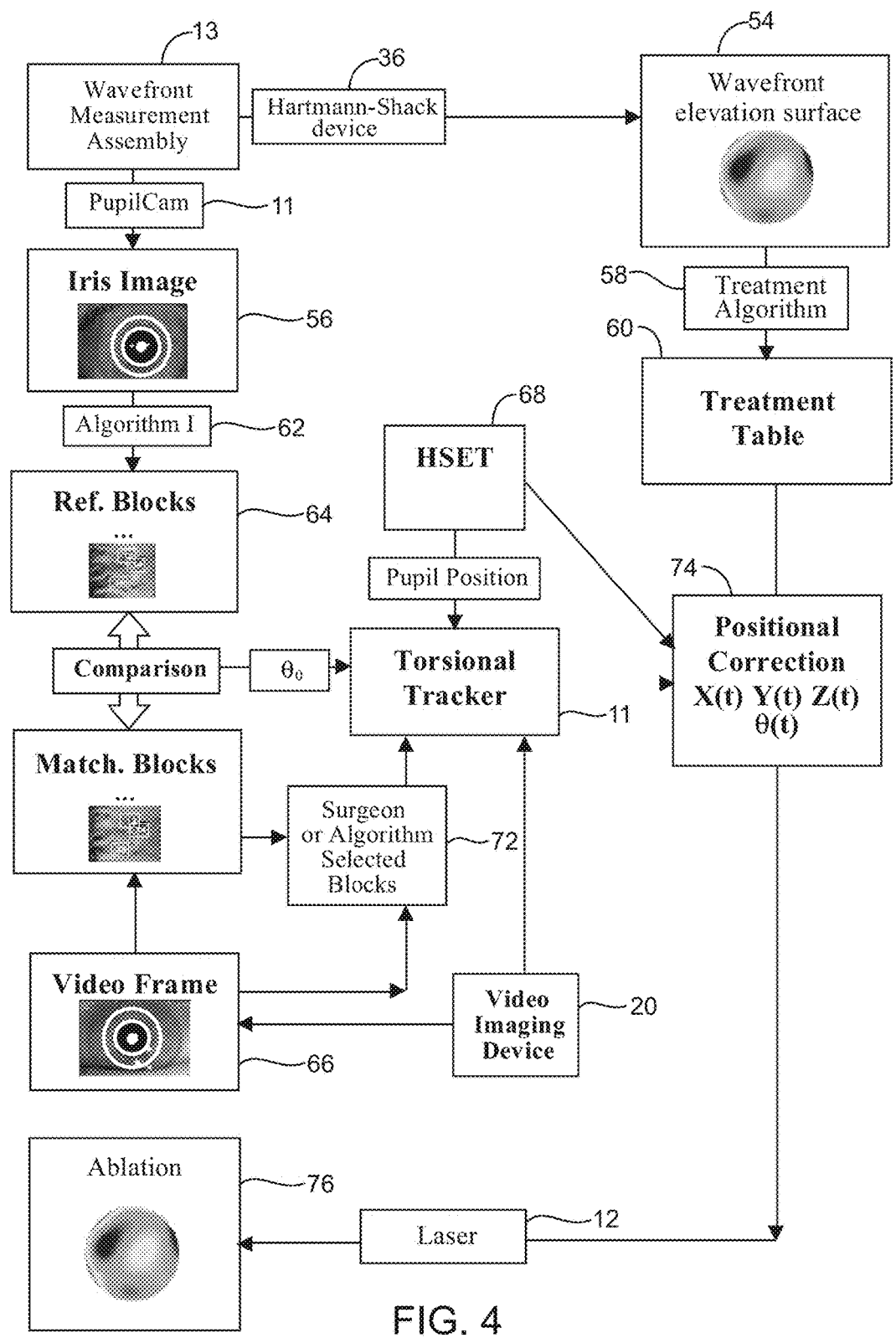
FIG. 4 schematically illustrates an exemplary system of the present invention.

Referring now to FIG. 4, an information flow of one embodiment of a method of the present invention will be described. Wavefront measurement assembly 13 can use wavefront sensors 36, such as Hartmann-Shack sensors, for obtaining a wavefront elevation surface 54 of the patient's eye. Wavefront elevation surface 54 can be run through a treatment algorithm 58 to generate a treatment table or ablation profile 60 that is customized to correspond to the patient's wavefront elevation surface 54. As noted above, ablation profile 60 can be calculated by a processor of wavefront device 10, laser system 15, or by a separate processor and stored in a memory of computer 17, 22.

During the calculation of the wavefront elevation surface, imaging assembly 11 can concurrently obtain an image 56 of the patient's eye, e.g., pupil and iris. The image of the patient's eye 56 can be analyzed by an algorithm 62 that locates the center of the pupil and/or iris, calculates the radius of the pupil and/or iris, and locates markers 64 in the patient's iris for subsequent registration and tracking.

In order to register the ablation profile 60 and the patient's eye during the laser treatment, the ablation pattern and the patient's eye should share a common coordinate system. Thus, ablation profile 60 should be positionally and torsionally aligned with the patient's eye when the patient's eye is positioned in the path of the laser beam. Additionally, the translational and torsional orientation of the patient's eye should be tracked during the surgical procedure to ensure an accurate delivery of the ablation profile.

To torsionally align (i.e., register) the ablation profile 60 with the patient's eye E, the reference or iris image 56 of the eye needs to have a unique coordinate transformation to an image of the eye taken by the pupil camera 20 of the laser system so as to determine the positional differences and torsional offset between the two images of the eye, $\theta_0$. In exemplary embodiments, pupil camera 20 is a video device that can obtain streaming video of the patient's eye. One frame 66 of the streaming video, typically the first frame of the streaming video, can be analyzed by the computer processor to locate the pupil center, iris center, and/or markers 64 that were originally located in the reference image 56. Once the pupil center, iris center, and/or markers 64 are located, a torsionally offset, $\theta_0$, between reference image 56 and video frame image 66 of the patient's eye is calculated.

Once the torsional offset $\theta_0$ is determined, the computer can track the translational position (x(t), y(t), and z(t)) of the patient's eye E with a high speed eye tracker (HSET) 68 and the torsional orientation ($\theta$(t)) of the eye with a torsional tracker 70. Because the position of the center of the pupil is tracked with the HSET 68, the torsional tracker 70 generally has to estimate the position of the markers 64 with respect to the pupil center.

If the HSET 68 determines that the patient's eye has moved (relative to video frame image 66), the computer can correct the delivery of the customized ablation pattern by adjusting the patient's customized treatment table 60 by adding in the translation and torsional measurements into the table. The treatment table can be adjusted such that at time t, if the overall rotation angle of the eye is $\theta$(t), and the next pulse of the laser is supposed to be delivered at location (x,y) on the cornea, the new location of the delivery of the pulse can be defined by:

$$\begin{pmatrix} x' \\ y' \end{pmatrix} = \begin{bmatrix} \cos\theta & -\sin\theta \\ \sin\theta & \cos\theta \end{bmatrix} \begin{pmatrix} x \\ y \end{pmatrix}$$

To track the torsional movement of the patient's eye, torsional tracker 70 can use the markers 64 identified above, other high-contrast iris patches, or if the patient's iris contains too little texture, the surgeon will have an option of drawing artificial landmarks 72 on the eye for tracking. Optionally, in some embodiments it is possible for the algorithm to decide if artificial markers are required.

The translational position and torsional orientation of the patient's eye can be tracked and analyzed by a computer processor in real-time so that the x(t), y(t), z(t) and $\theta$(t) information 74 can be used to adjust the customized treatment table 60 so that laser 12 delivers the appropriate ablation pattern 76 to the patient's eye.

Some exemplary methods of carrying out the present invention will now be described. As described above, a first step of the present invention entails registering a reference image of the eye taken during the calculation of the wavefront elevation map with a second image of the eye taken just prior to the delivery of the ablation energy.

Figure 5:
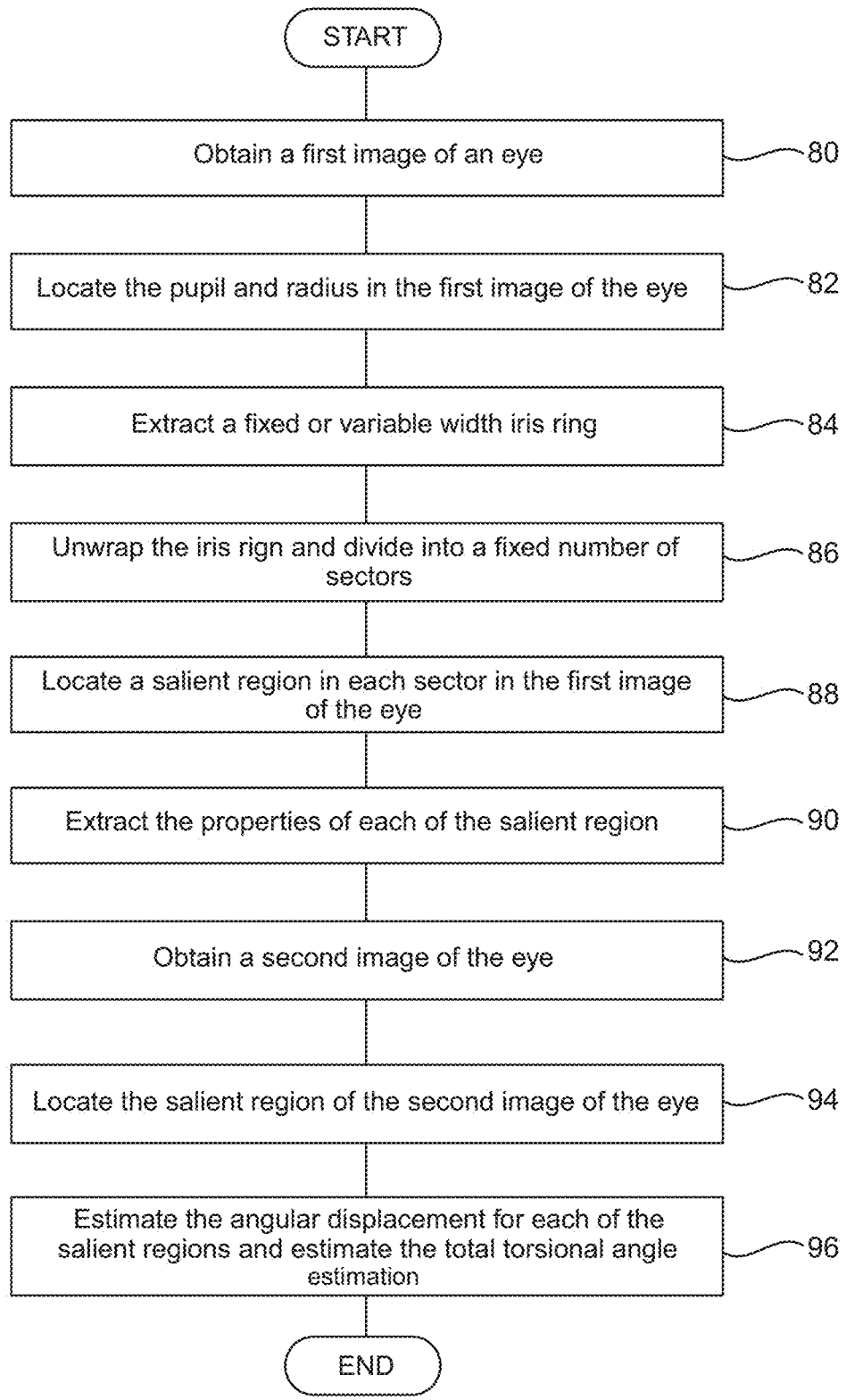
FIG. 5 schematically illustrates a method of the registering a first image with a second image.

FIGS. 5 to 9 illustrate aspects of one embodiment of a method of the present invention. FIG. 5 schematically illustrates the data flow through an alignment algorithm that can torsionally register a reference image with a second image of the eye to determine the torsional displacement between the two images of the eye. An initial step in the method is to obtain the first, reference image. (Step 80). As shown in FIG. 6A, in one embodiment, the first or reference image is a grayscale image of the patient's eye that is taken by a CCD camera in the wavefront measurement device under infrared illumination ($\lambda$=940 nm). In one test configuration, the images were 768×576 pixels and have 256 gray levels. The image contains the pupil and the iris. In some images, part of the iris may be occluded by one or both of the eyelids or cropped by the camera's field of view.

It should be appreciated however, that the present invention can use a variety of imaging devices to produce different images and can be illuminated under various types of illumination.

In most configurations, the smallest distance between the edge of the pupil and the obstructing elements, such as eyelids, eyelashes, strong shadows or highlights should be sufficiently large to leave a portion of the iris completely exposed for the entire 360-degree range. Preferably, the largest possible portion of the iris is in sharp focus so as to expose its texture.

A pupil finding algorithm can be used to locate the pupil, calculate the radius of the pupil and find the center of the pupil (Step 82). In one embodiment the pupil is located by thresholding the image by analyzing a pixel value histogram and choosing the position of a first "dip" in the histogram after at least 2000 pixels are below the cutoff threshold. All pixels below the threshold are labeled with "1" and pixels above the threshold are labeled with "0". Pixels labeled with "1" would generally correspond to the pupil, eyelashes, and possibly other regions of the image. It should be appreciated however, that the number of pixels employed will be related to the area of the pupil and will vary with applications of the invention.

The two distinguishing features about the pupil region, compared to other non-pupil regions is its large size and central location. In some embodiments, regions intersecting with a 5-pixel wide inner frame of the image can be discarded and the largest remaining region can be selected as the pupil.

If desired, the selected pupil region can be filled to remove any holes created by reflections, or the like. For example, in one embodiment, the remaining region of the image may also be analyzed for convexity. If the ratio of the area of the region to the area of its convex hull was less than 0.97, a circle completion procedure can be applied to the convex points on the region's boundary. One way of performing such an analysis is through a Matlab function "imfeature( . . . , 'CovexHull')". A radius and center of the pupil can be estimated by a standard weighted least-square estimation procedure. If the convexity quotient was above 0.97, the radius and centroid can obtained using conventional methods, such as Matlab's "imfeature( . . . , 'Centroid', 'EquivDiameter')" function.

Optionally, in some embodiments an iris finding algorithm can be used to locate the iris, calculate the radius of the iris, and/or locate the iris center. Since the images of the eye from both imaging assembly 11 and the camera 20 both contain the pupil and iris, in some embodiments it may be more accurate to register the images by calculating the center of the pupil and the center of the iris and expressing the position of the pupil center with respect to the center of the iris. The center of the iris may be described as a center of a circle corresponding to the outer boundary of the iris. The position of the center of the iris can be used to calculate a pupil offset from the iris center.

If $\overrightarrow{X_P^{WS}}$ are the coordinates of the center of the pupil in image 56 (FIG. 4). Let $\overrightarrow{X_I^{WS}}$ be the center of the iris in image 56. Let $\overrightarrow{X_P^{LASER}}$ be the center of the pupil in the laser's camera image 66. Let $\overrightarrow{X_P^{LASER}}$ be the center of the iris in the laser's camera image. Even if the iris or pupil are not circular (e.g., elliptical) there will still be a center for each of the pupil and iris. Then, the center position $\vec{C}$ with respect to pupil center for the surgery can be defined as:

$$\vec{C} = \overrightarrow{X_I^{WS}} + \overrightarrow{X_P^{WS}} + \overrightarrow{X_P^{WS}} - \overrightarrow{X_P^{LASER}} + \overrightarrow{X_I^{LASER}}$$

Figure 6A:
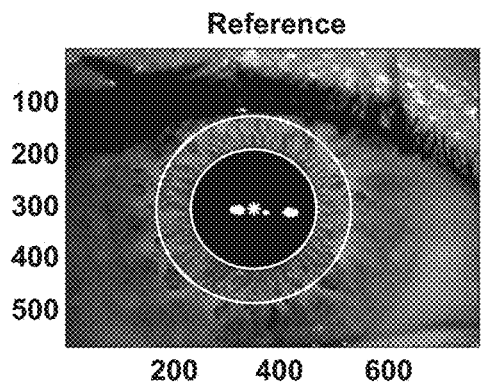
FIG. 6A illustrates a reference image of an eye.
Figure 6B:
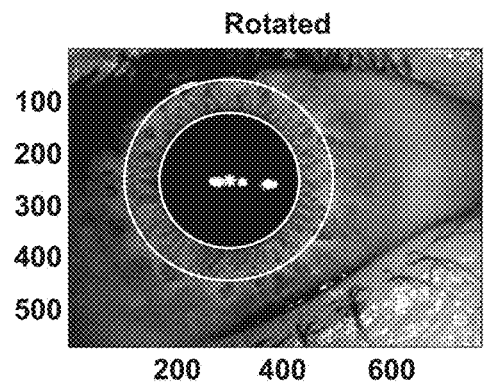
FIG. 6B illustrates a rotated image that corresponds to the reference image of FIG. 6A.
Figure 6C:
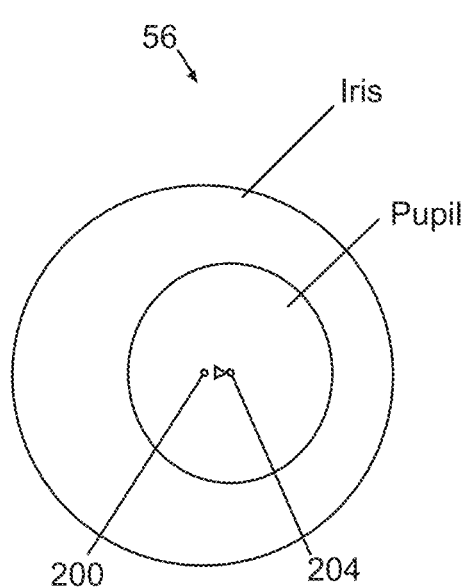
FIGS. 6C and 6D illustrate a center of a pupil and center of an iris.
Figure 6D:
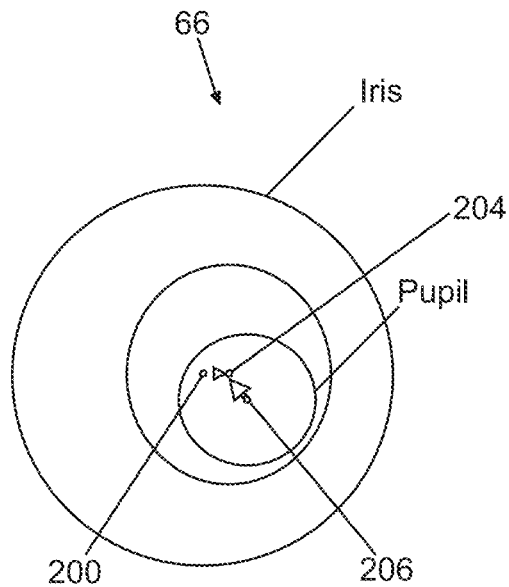

FIGS. 6C and 6D schematically illustrate simplified images of the eye taken with image assembly 11 and camera 20, respectively that can be analyzed to find the pupil center and iris center. Marker 200 marks the iris center in both images, marker 204 corresponds to the pupil center in image 56 and marker 206 corresponds to the pupil center in the laser image 66. As illustrated in the images, in laser image 66, the pupil has changed in size (as shown by the gray outline) and the center of the pupil has moved relative to the center of the iris 200. In some embodiments, during laser surgery, the measured wavefront measurement and corresponding ablation pattern can be centered over center position $\vec{C}$ that is calculated by the above equation.

Since the boundary of the iris may be soft in terms of contrast and may also degraded by shadows and light reflections, there may be difficulties associated with detecting the outer iris boundary in infrared images of the eye. One method for detection of both iris and the pupil in the image I(x,y) is to minimize the following integral over all possible values of iris radius and center:

$$\max_{(r,x0,y0)} \left| G_\sigma(r) * \frac{\partial}{\partial r} \oint_{r,r0,y0} \frac{I(x, y)}{2\pi \cdot r} ds \right|$$

Figure 6E:
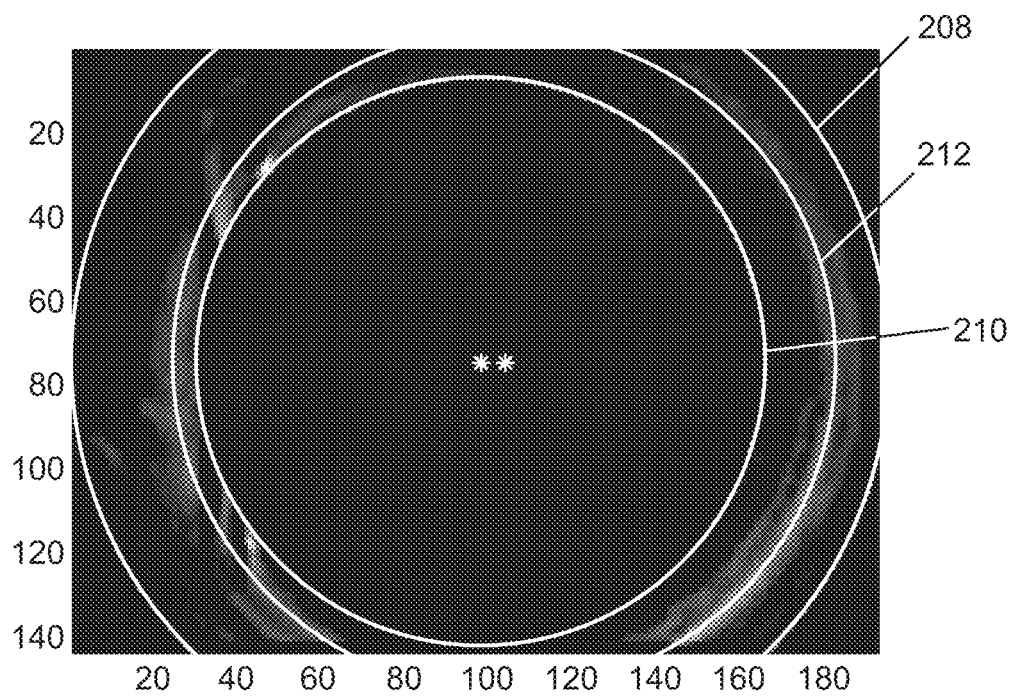
FIG. 6E illustrate an inner and outer radii of a range of the iris radii.

One alternative to the above method takes advantage of the fact that the pupil center has already been found (as described above), that the iris has a limited range of possible values and the iris center is usually not very far from the pupil center. As shown in FIG. 6E, since the center of the pupil and the center of the iris are not far from each other, it is possible to estimate the radial derivative of the image intensity with respect to the iris center by the radial derivative with respect to the pupil center. Furthermore, the limited range of iris radius values occurring in nature, allows restriction of a range of possible search to a ring centered at pupil center and having inner and outer radii such that the iris edge should always be located somewhere within the range. In one embodiment, the numerical search range, can be between approximately 10.5 mm and 14 mm. In other embodiments, the range may be larger or smaller, if desired. See Burns et al., IOVS, July 2002.

For example, as illustrated in FIG. 6E, circles 208, 210 illustrate a potential range for the iris radius. The values of the radial derivative that exceed certain threshold can be passed to the weighted least square estimator for the best circle fit through the set of points, as is described herein. The initial weights of the points are proportional to their intensity. After enough iterations (e.g., two iterations) are performed to converge to a stable solution, the algorithm converges to the answer represented by the red circle.

The iris finding algorithm shows tolerance to other edges detected by the derivative operator, but corresponding to other structures in the image (e.g., LASIK flap). If desired, to reduce the computation time, the original images can be smoothed with a Gaussian kernel and sub-sampled by a factor of four prior to a derivative computation.

In embodiments of the present invention, the boundary of the iris can be localized with sub-pixel accuracy, but it might be slightly displaced from its true location if the shadows in the image soften the boundary edge. However, the errors are fairly well balanced in all directions from the center, so that the final result is very close to the actual center.

In the embodiments tested, the image scale for both the second image (e.g., laser image) and the first image (e.g., wavefront image) is estimated to be 52.3 pixels per millimeter, which is 19.1 µm per pixel. An error of one pixel in the boundary estimation on one side of the iris would result in about 10 µm error in the estimate of the iris center. Given the current precision of conventional eye trackers (about 50) and the range of pupil center shift (up to 1000 µm), the errors of a few pixels in the iris boundary would still be within the acceptable accuracy for the ablation centering.

Next, after the pupil center (and/or iris center) are located, a width of the iris ring can be extracted from the images. (Step 84). The iris can be treated as an elastic sheet stretched between pupil and the outer rim of the iris. In embodiments that do not use the iris finding algorithm, the width of the iris band can be set to 76 pixels for images of dark-colored eyes, and 104 pixels for the light-colored eyes. It should be appreciated, however, that other width estimations can be used. The radius of the iris in the reference images of FIGS. 6A and 6B were estimated to be 320 pixels and assumed to be roughly constant for all people.

Figure 7A:
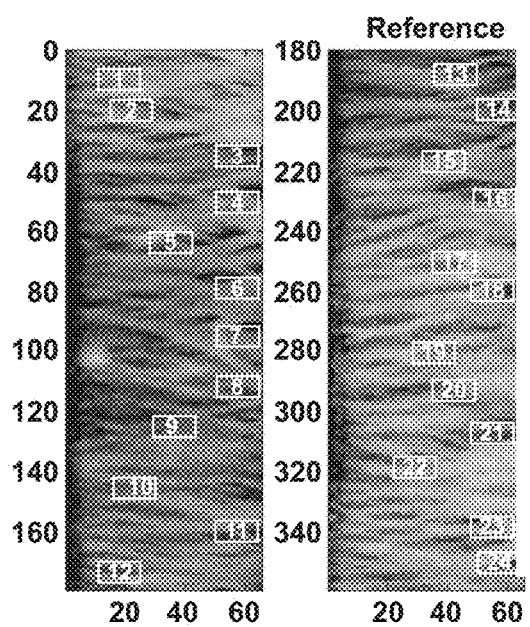
FIG. 7A illustrates an unwrapped iris that is segmented into 24 sectors, with each sector having a numbered marker.

As shown in FIG. 7A, the iris ring can then be unwrapped and divided into a fixed number of sectors, by converting the Cartesian iris coordinates into polar coordinates, centered at the pupil. (Step 86). In alternative embodiments, it may be possible to analyze the iris ring without unwrapping it. However, Applicant has found that unwrapping and scaling the iris ring allows better matching of texture blocks between different images of the eye by means of pure translation. For example, as shown in FIGS. 7C and 7D, if the iris ring is not unwrapped, the software may have trouble matching of texture blocks that have rotated (FIG. 7C), whereas if the iris ring is unwrapped, the texture blocks have the same relative shape (FIG. 7D).

In some embodiments, the iris ring can be sampled at one-pixel steps in the radial direction for the reference image. Optionally, to reduce aliasing, the images can be smoothed with $\sigma=1$ pixel Gaussian kernel.

Optionally, the dynamic range of pixel values in the iris may be adjusted to remove outliers due to reflections from the illumination LED lights. The pixel value histogram can be thresholded so that all the pixels with values above the threshold are assigned the value of the threshold. Also, some band-pass filtering may be applied to the iris bands prior to region selection to remove lighting variation artifacts.

After the iris is divided into sectors, one salient region or marker in each sector in image can be located and its properties can be extracted. (Steps 88, 90). In one embodiment, the iris region is segmented into twenty four sectors of fifteen degrees. It should be appreciated, however, that in other embodiments, the iris region can be segmented into more than twenty four sectors or less than twenty four sectors.

The markers in the reference image can be stored and later located in the second image of the eye so as to estimate the torsional displacement of the eye between the two images. One embodiment of a method of locating the markers is described more fully in Groen, E., "Chapter 1 on Video-oculography," PhD Thesis, University of Utrecht (1997), the complete disclosure of which is incorporated herein by reference.

The markers should be sufficiently distinct and have high contrast. There are several possible ways to select such points. In one implementation, a square mask of size M×M (for example, 21×21 for dark-colored eyes and 31×31 for light-colored eyes) is defined. The mask can be scanned over each of the twenty four sectors, and for each pixel in each sector a value is computed from the region inside the mask centered at that pixel. The value assigned to the pixel is determined as the sum of amplitudes of all spatial frequencies present in the region. In one embodiment, the sum of the amplitudes can be computed by a Fourier transform of the region. If desired, the central 5×5 portion of the Fourier spectrum can be nulled to remove a DC component. The maximum value can then be located in each sector, such that the boundary of its corresponding mask is at least 5 pixels away from the iris image boundary in order to avoid getting close to the pupil margin and other boundary artifacts, such as the eyelid and eyelashes. The "winning" positions and the corresponding blocks are stored for later comparison.

It should be appreciated, however, that there are alternative methods for evaluation of block/marker texture strength. For example the following matrix can be applied. If Gx is the derivative of the block intensity in the x-direction, and Gy is the derivative of the block intensity in the y-direction, then:

$$Z = \begin{bmatrix} \sum Gx^2 & \sum GxGy \\ \sum GxGy & \sum Gy^2 \end{bmatrix}$$

And let $\lambda_1$, $\lambda_2$ be the eigen values of the matrix of Z, with $\lambda_2$ being the smaller one, then $\lambda_2$ is the texture strength of the block.

The second image of the eye can also be obtained. (Step 92; FIG. 6B). In exemplary embodiments, the second image is obtained with a laser surgical system's microscope camera prior to delivering the ablative energy to the patient. In one configuration, the laser camera has a resolution of 680×460 pixels using 256 grayscale levels. The magnification of the laser camera in relation to the reference camera from the CCD camera was estimated to be 0.885. The eye can be illuminated by a set of infrared LED lights having a wavelength of 880 nm. It should be appreciated, however, that many other imaging devices can be used to obtain different image types, including images that do not require a magnification, images of different resolution, and images that are illuminated by other light wavelengths.

Figure 7B:
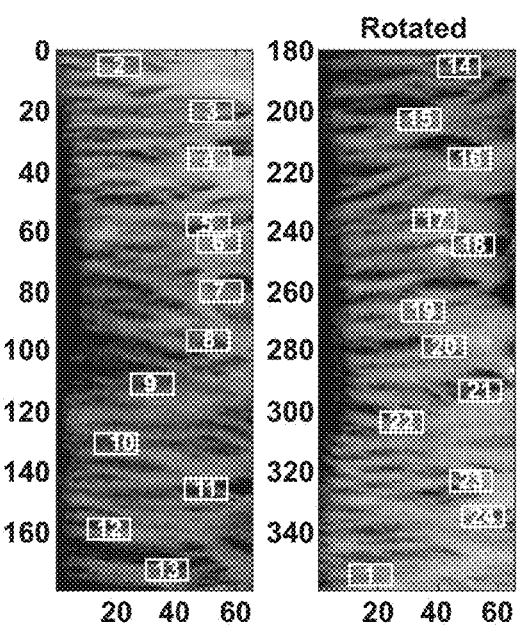
FIG. 7B illustrates a corresponding unwrapped iris in which the markers are torsionally rotated from their original positions.

The sectors in the second image are located and the salient regions that correspond to the salient regions in the reference image are located. (Step 94; FIG. 7B). For each sector in the second image, a best matching region is located. Optionally, the search is constrained to the matching sector and the two adjacent sectors in the second image, thus limiting possible matches to within 15 degrees, which is a reasonable biological limit for ocular cyclo-rotation. It should be appreciated however, in other embodiments, the range of limiting the possible match may be larger or smaller than 15 degrees.

Figures 8A, 8B:
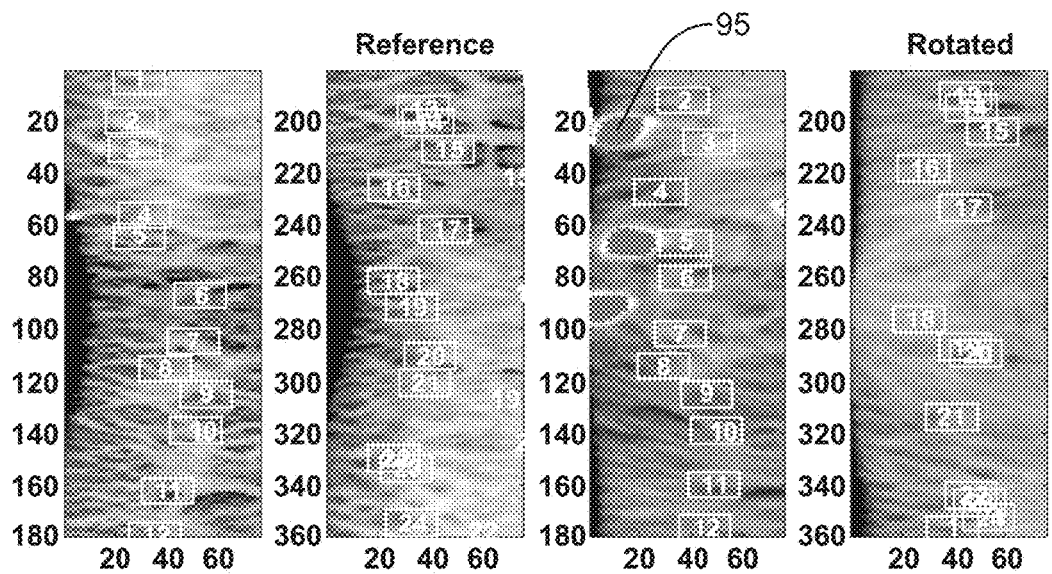
FIG. 8A illustrates an unwrapped iris.
FIG. 8B illustrates an unwrapped iris with LED reflections.

The match between the marker in the reference image and the marker in the second image is evaluated as the sum of absolute errors (after both blocks are made to have zero mean value) for each corresponding region centered at a given pixel. As shown in FIGS. 8A and 8B, due to presence of LED reflections on the iris, some portions of the iris may lose its texture in the second image. In some embodiments, these areas 95 can be detected by histogram analysis similar to pupil detection and can be excluded from matching. The points with the smallest error can then be selected as the matching markers for each marker in the reference image.

Alternatively, instead of using the sum of absolute errors to match the markers, a dot product of the mean-subtracted reference and the second image patches can be calculated, where:

$$L = \sum_i (I_i - \bar{I})(J_i - \bar{J})$$

in which the higher the "L", the better the match between the markers.

Figure 9:
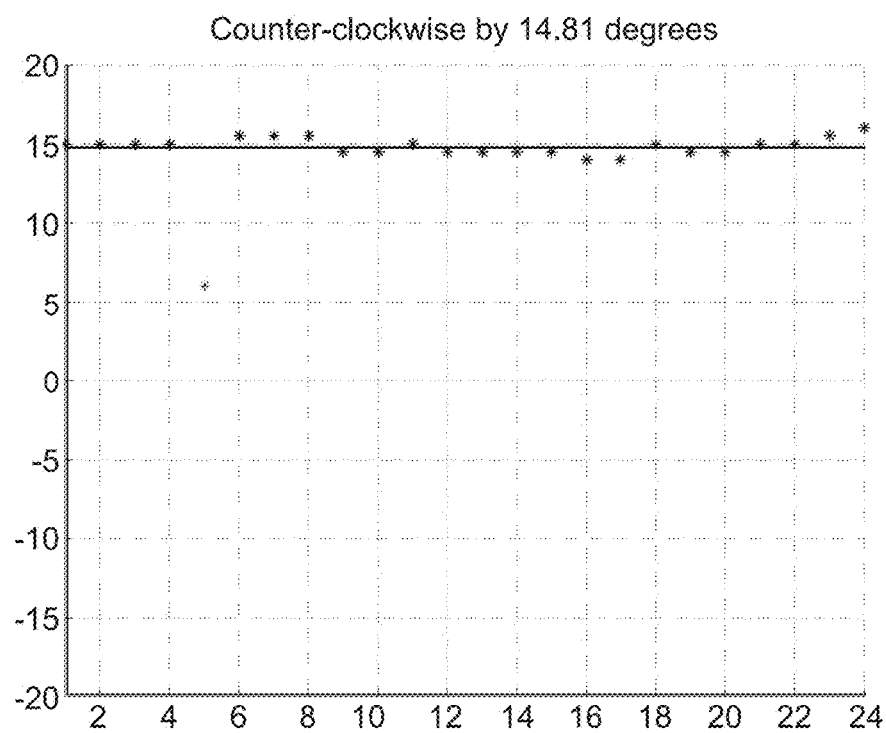
FIG. 9 is a graph that illustrates an angular rotation of the 24 markers.

Once the corresponding salient regions/markers are located in the second image, an angular displacement for each marker is calculated to estimate a total torsional angle of the eye between the first, reference image and the second image. (Step 96; FIG. 9).

Under ideal circumstances, the displacement of each marker would be identical and equal to the torsional angle. However, there are several distortions that make the problem of estimating the true torsional angle more complex. First, the center of the pupil may not be estimated correctly. This introduces a sinusoidal distribution of displacement angles around the true torsional angle. The amplitude of the sinusoid is usually quite small. Second, the actual shape of the pupil is often elliptical and not round. This can introduce a sinusoidal distortion with twice the period of the center of the pupil distortion due to the method of measurement of the landmarks with respect to the circular pupil. Indeed, points further away from the pupil center will be spaced closer to each other after the iris is unwrapped, and points closer to the pupil center would end up being spaced more widely. Finally, some corresponding markers may make false matches; such markers can be treated as outliers. Consequently, to account for such distortions, in one embodiment the estimated angles can be fitted with a number of different functions using an iterative weighted estimation as follows:

$F1 = TA1$ $F2 = TA2 + A1*\sin(\theta) + B1*\cos(\theta)$ where TAs are the estimates of the true torsional angle and θ is the angular coordinate of the markers. Application of the functions to the torsional angle data can thereafter provide an estimate for the torsional angle $\theta_0$ between the reference image and the second image.

The initial torsional angle, $\theta_0$, computed by the alignment algorithm (between the iris image 56 taken with pupil camera 13 and the initial video frame 66 from imaging device 20) can be added to every subsequent frame for tracking of the torsional orientation of the patient's eye. The total torsional orientation $\theta_{total}$ (t) of the patient's eye in the laser image can be described as follows:

$$\theta_{total}(t)=\theta_0+\theta(t)$$

where θ(t) is the measured torsional angle between the eye in the initial frame of the video stream and the eye in the $n^{th}$ frame at time t.

While the alignment algorithm that calculates $\theta_0$ does not have to produce results in real time, a tracking algorithm that tracks the torsional rotation θ(t) of the eye should work at frame rate, which demands quick, efficient and accurate computations. In one embodiment, the high speed eye tracker (HSET) of the laser surgical system can be used to keep track of the translation of the pupil in the x, y, and z directions. Having the position of the pupil readily available requires only that the torsional tracker estimate the positions of the iris landmarks with respect to the center of the pupil.

The iris can undergo rigid translations (e.g., movement in the x, y, and z directions), rotations, as well as some non-rigid affine transformations of scaling and shearing. While the torsional angle is not affected by the non-rigid transformations, it is preferable that the non-rigid transformations be taken into account in order to ensure accurate feature matching from frame to frame. In one method, the main ideas is that given image $I_0$, a feature portion of a frame at time t=0, and image $I_n$, part of frame at time t=n, one can determine the optimal set of parameters A and d, such that:

$$I_n(Ax+d)=I_0(x)$$

where A=1+D, where D is a deformation matrix and d is the translation of the feature window. Such an approach is described in computer vision literature such as Lucas B. D. and Kanade, T. "An Iterative Image Registration Technique and Application to Stereo Vision" ILCAI (1981); Shi, J. and Tomasi, C. "Good Features to Track," IEEE Conference on Computer Vision and Pattern Recognition, 1994; and Hager, G. D. and Toyama, K. "X-Vision: A portable Substrate for Real-Time Vision Applications," Computer Vision and Image Understanding, 1996, the complete disclosures of which are incorporated herein by reference. Parameters of deformation and translation are determined by Newton-Raphson minimization procedure which can produce accurate results.

Since the types of transformation that occur during laser eye surgery are primarily translation (x, y, z) and torsional rotation about the optical axis of the eye, these parameters can be estimated and the remaining scale and shear parameters are refined afterwards. Such a procedure has been found to be robust in recovering the actual motion and avoids excessive deformations that might mimic the observed data.

Figure 10:
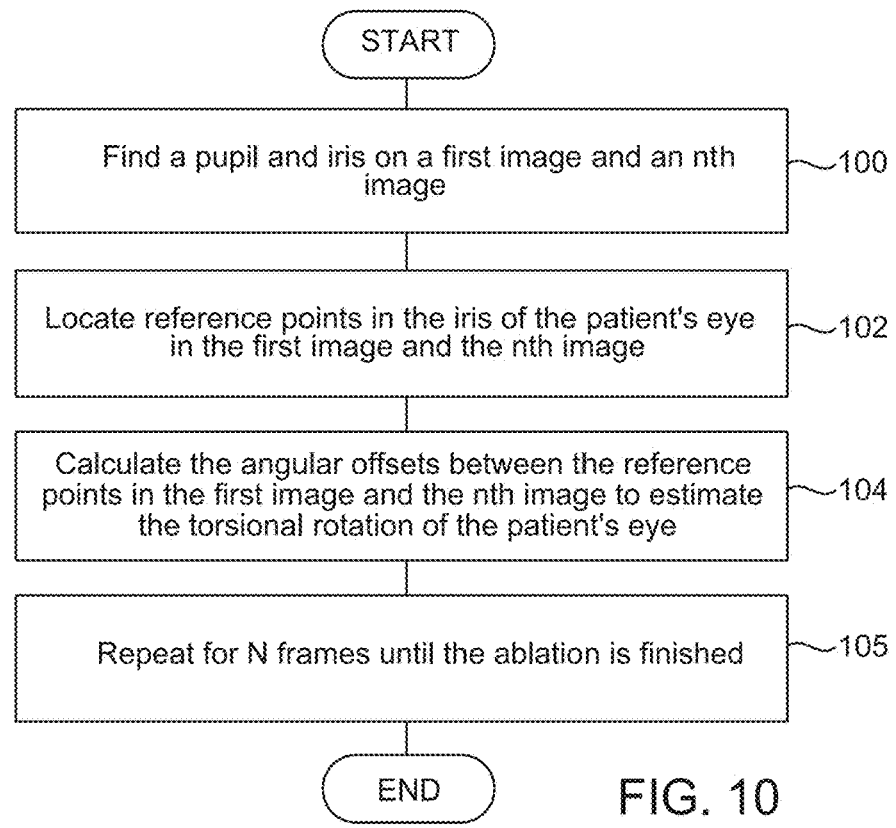
FIG. 10 is a simplified method of tracking a torsional rotation of a patient's eye.

FIG. 10 schematically illustrates a simplified method of tracking the torsional rotation of the patient's eye during the surgical procedure. First, the pupil and iris are located in both the first frame and $n^{th}$ frame of the video stream. (Step 100). Reference points can be located in the first frame and the corresponding reference points can be located in the $n^{th}$ frame of the video stream. (Step 102). The angular offset between the reference points in the two images can then be calculated to estimate the torsional rotation of the eye. (Step 104). The steps can be repeated for each of frames of the video stream until the ablation procedure is completed. (Step 105).

Figure 11:
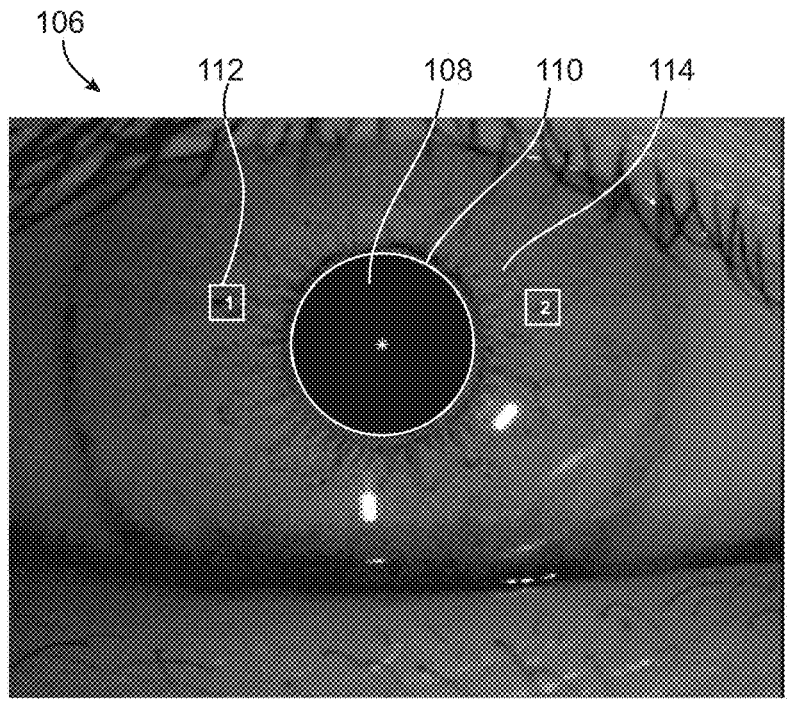
FIG. 11 is a frame image of a patient's eye and two markers on the iris that are used for tracking a torsional rotation of the patient's eye.

FIG. 11 is an example of a first frame 106 from the video stream of the eye taken prior to the laser ablation. A pupil 108 has been located (as noted by circular outline 110 image around the circumference of the pupil), and two reference loci or points 112, 114 are selected for torsional tracking. Generally, reference points 112, 114 are a subset of the points chosen for registration (described above). The points 112, 114 can be chosen automatically by the software of the present invention based on its texture strength, and positioning relative to the pupil (e.g., 8 o'clock position and 2 o'clock position). In alternative embodiments, however, it may be possible to independently select points 112, 114 separate from the original markers using the same technique described above or to manually select or draw the reference points 112, 114 on the patient's iris.

The process of selecting points for tracking can be automatic or surgeon-assisted. The automatic process can select one point on the right of the pupil and one on the left based on which reference block in the corresponding neighborhood has best block-match score and also included in the estimate of the alignment angle, i.e. not an outlier. If the texture of the iris has very low contrast or does not have distinctive components, it may be necessary to introduce artificial landmarks. Such landmarks can be drawn on the eye by the surgeon, so that the algorithm would track their spatial displacements instead of displacements of the patches of iris texture.

One exemplary selection algorithm selects a subset of blocks that are not outliers. From this subset, blocks are removed that are in the positional domain of possible reflections. These positions are known due to specific placement of LEDs on the laser. The texture of the remaining blocks from the laser image may be quantified by the second largest eigenvector $\lambda_2$. Two blocks, roughly on the opposite sides of the pupil are chosen, such that they have the largest $\lambda_2$ in the group. In one embodiment, the "left block" is selected from the valid blocks centered around the 8-o'clock position, and the "right block" is selected among the valid blocks centered at the 2-o'clock position. The coordinates of the centers of these blocks can be used to initialize tracking.

Once the blocks/loci 112, 114 have been selected in the first frame, for each consecutive frame of the video feed, the blocks are located within a region of the iris that has the same position with respect to the pupil of the eye. The region is generally limited to approximately 15 degrees, since the eye will generally not rotate more than such a range, and within such a time between each consecutive frame of the video stream, the torsional rotation will likely be much less than the 15 degrees. As can be appreciated, in other embodiments, the range of analysis can be limited to a smaller or larger range, if desired.

The spatially corresponding regions of the first frame and the $n^{th}$ frame can be compared for affine displacement, giving preference to rigid transformations. In one embodiment, only horizontal and vertical displacements are reported by the tracking algorithm.

Figure 12:
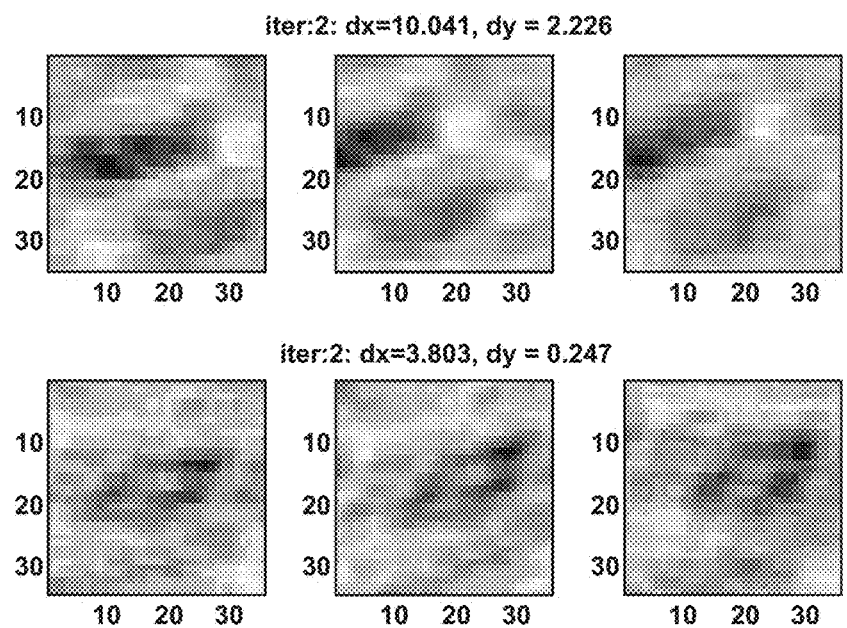
FIG. 12 illustrates six reference blocks/markers of the patient's iris that are used to track the torsional rotation of the patient's eye.
Figure 13:
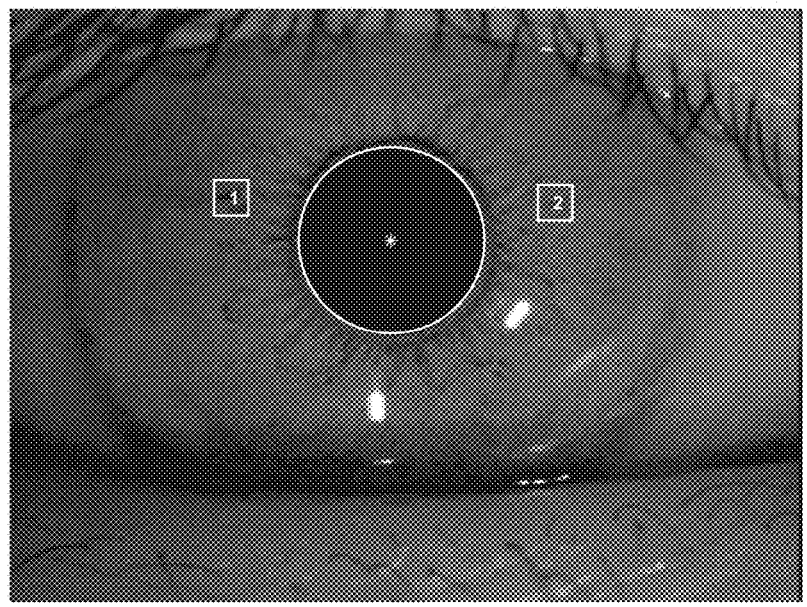
FIG. 13 illustrates the relative positions of the reference markers relative to the center of the patient's pupil.

FIG. 12 illustrates six images of selected blocks 112, 114. Images 116, 118 are images of blocks 112, 114 in reference image 66. Blocks 120, 122 are the corresponding blocks from the new, real-time frame. Block images 124, 126 are the best transformed block from the first frame that match the target block. From the change in the positional coordinates of the blocks 112, 114, a torsional angle between the first frame and the second frame can be computed (FIG. 13).

One exemplary method of calculating the torsional angle between the two selected block images in image frames of the video feed will now be described. If $B_i$ is the coordinate of the $i^{th}$ block in the reference frame, X is the pupil center coordinate in the reference frame, and $X_n$ is the pupil center coordinate in the $n^{th}$ frame, then the expected coordinates of the blocks in the $n^{th}$ frame are:

$$B_{in} = B_i - X + X_n.$$

The expected pupil center coordinates of the blocks in both frames are:

$$B_i = B_i - X$$

If $D_i$ is the translation vector that aligns the $i^{th}$ block contents between the two frames, the correct block locations in the new frame are:

$$B'_i = B_i - D_i$$

The angular position of each block in the pupil centered reference frame is described by $\theta_i = \tan^{-1}(B_y/B_x)$ and the total torsional angle between the $n^{th}$ and the reference frame is:

$$\theta_n = \text{mean}_i(\theta'_i - \theta_i)$$

where $\theta'_i$ is the angular position of the block in the nth frame and $\theta_i$ is the angular position of the block in the reference (first) frame.

It should be noted that in FIGS. 11 and 13, the two frames are at different levels of illumination, but the algorithm of the present invention is robust enough to overcome this difference. In general, if possible, t is preferred to maintain the same level and source of background illumination in the range of camera sensitivity in order to achieve accurate tracking. Typically, the conditions during the laser eye surgery fall into this category and there are very few changes from frame to frame.

As noted above, one part of the described embodiment of the tracking algorithm is to estimate the motion parameters of a given block or marker. If I is the block in the original frame and J is the spatially corresponding block in a subsequent frame, let x be the pixel coordinates in these blocks. To estimate an affine transformation matrix A and translation vector D, the following equation can be minimized:

$$O(A, D) = \sum_x (I(Ax + D) - J(x))^2$$

Matrix A can be decomposed into a rotation component and a scale/shear component as follows:

$$A = \begin{bmatrix} 0 & \alpha \\ -\alpha & 0 \end{bmatrix} + \begin{bmatrix} sx & \gamma \\ 0 & sy \end{bmatrix}$$

By estimating the rotation component of the matrix A and the translational vector D, the number of parameters can be reduced from 6 to 3. This approach clarifies between several possible solutions towards the one that has only rigid motion. While scaling and shear may occur as a result of pupil size change, their contribution to motion should be very small.

A linear system for computing rigid motion parameters is:

$$\sum_x \begin{bmatrix} GxGx & GxGy & GxGr \\ GyGx & GyGy & GyGr \\ GrGx & GrGy & GrGr \end{bmatrix} * \begin{bmatrix} D \\ \alpha \end{bmatrix} = \sum_x \begin{bmatrix} Ho & Gx \\ Ho & Gy \\ Ho & Gr \end{bmatrix}$$

where $$Gx(x) = \frac{\partial}{\partial x} I(x) * w(x)$$

$$Gy(x) = \frac{\partial}{\partial y} I(x) * w(x)$$

$$Gr(x) = \left( y \frac{\partial}{\partial x} I(x) - x \frac{\partial}{\partial y} I(x) \right) * w(x)$$

$$Gx(x) = (I(x) - J(x)) * w(x)$$

where $w(x)$ is an optional weighting functions. Because the equations above are approximations, iterative Newton-Raphson minimization can be used to solve the system.

Experimental Registration Results:

Experimental results for the alignment algorithm which registers the reference image of the patient's eyes with the second image of the patient's eye was obtained using Matlab software. The accuracy of the fit was determined by several factors: (1) the number of point used in the fit (at least half (12) of the reference points had to be used), and (2) the RMS error of the fit (1 degree was the highest RMS error allowed); and (3) a visual inspection of the matching reference points and the measurements taken with protractor were used to confirm the estimate. The original set of experiments was conducted with the laser camera magnification factor of 0.885. All the images of dark-colored eyes gave accurate predictions of the torsion angle by at least one of the methods. However, the light-colored eye did not have sufficient texture at that magnification to have a reliable torsion angle estimate.

Figure 14:
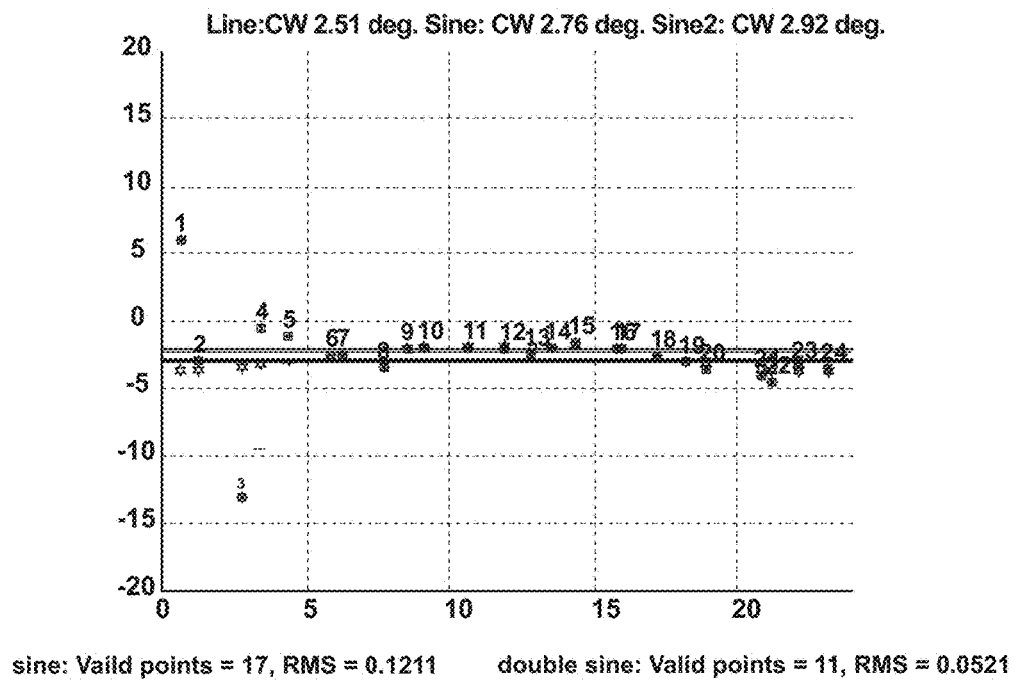
FIG. 14 illustrates torsional angle estimates for an eye having a dark-colored iris.
Figure 15:
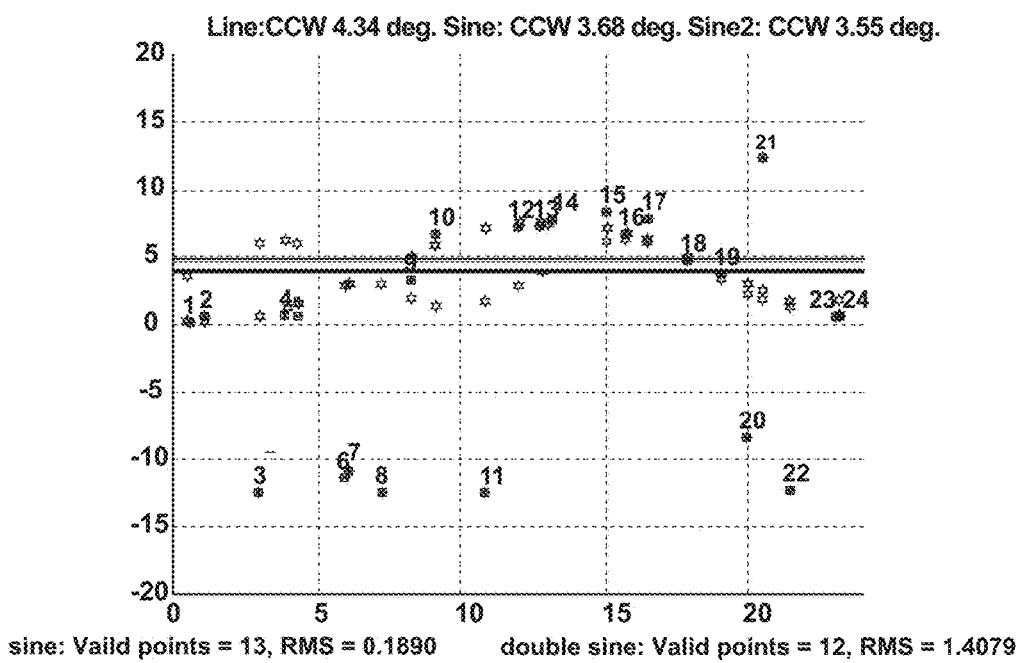
FIG. 15 illustrates torsional angle estimates for an eye having a light colored iris.

In a second hardware configuration, the magnification factor of the laser's camera was adjusted to match that of the imaging device of the wavefront measurement device, thus eliminating scaling issues. Also, as the resolution of the laser camera increased due to larger magnification factor, more details became visible on the light-colored irises. Sixteen eyes (from six people) were photographed with the a CCD of the VISX WaveScan™ camera, while subjects were in the sitting position and with the laser's camera, while subjects were laying down in the surgical chair. The torsional angle was estimated between the two photographs of the same eye of the same subject. FIG. 14 is a torsional angle estimate for two different dark-colored iris eyes. FIG. 15 is a torsional angle estimate for two different light-colored iris.

The estimates in FIG. 14 are all within ½ degree from each other and the one providing the best fit is the sinusoidal fit with 17 points used and RMS=0.21. In FIG. 15 the estimates are less similar, but the best estimate is again a sinusoidal fit with 13 points and RMS=0.18 that captures the correct match points.

The line fit criteria is not explicitly evaluated, since it can be thought of as a sinusoidal fit of zero-amplitude. This is simply a result of having 3 parameters in the sinusoidal fit (mean, amplitude and phase) versus one parameter for the line (mean). Therefore, any line fit quality would be worse than the sinusoidal estimates, even if it captures the nature of the data. As mentioned earlier, the line fit estimate of the torsion angle is usually close to the value reported by sinusoidal or possibly a double sinusoidal fit. FIGS. 16A and 16B summarize the results for the data set processed by the algorithm.

While not required, it is desirable that while capturing the reference image with imaging device 13, the following points should be considered. First, a majority of the iris should be visible so that a minimum width of the iris ring is more than 80 pixels. Second, the focus of the camera should be adjusted so that most of the iris is in focus providing the highest possible texture resolution of the iris ring. Several images can be taken to ensure good quality. Third, images with strong shadows and reflections on the iris should be rejected in order to avoid strong false markers. Finally, images should be saved into a file of type BMP or TIF. Optionally, image names should contain unique name of the subject, left or right indicator for the eye and the ID of the device from which they come (e.g., laser image or wavefront image).

While capturing the laser image the same reference points should be considered. As such, the illumination when obtaining the wavefront image should be the same when obtaining the image with the laser camera. Applicants have found that dark-colored eyes have more rich texture under the infrared illumination and light-colored eyes have more rich texture under visible light. The striated trabecular meshwork of elastic pectinate ligament (anterior layer) creates a predominant texture under visible light. For the near infrared light, deeper slower modulated stromal features dominate the iris pattern. See for example Daugman, J. "High confidence visual recognition of persons by a test of statistical independence," IEEE Transactions of Pattern Analysis and Machine Intelligence, vol. 15(11), pp 1148-1161 (1993).

Image quality may also be degraded by LED reflections. However, because illumination is required, it may be unavoidable to have several LED reflections on the iris. These features can be handled by the algorithm as described above. These reflections, however, can greatly degrade the image quality. As shown in FIG. 17A, the shadow makes it impossible to discern any texture of the right side of the iris. As a result, as shown in the FIG. 17B, the alignment data obtained from the image in FIG. 17A was rejected due to the large RMS factor (i.e., above 1). Therefore, the alignment algorithm of the present invention can have an internal quality of fit check that automatically rejects bad data.

In order to make the alignment system work under real surgical conditions, the system should be robust to noise and distortions introduced by cutting and lifting of the LASIK flap, dried surface of the cornea and other factors. In order to achieve this robustness, three additional steps can be added to the alignment algorithm. A first step was to mark the expected position of the LASIK flap as an invalid region, preventing the algorithm from selecting reference blocks in that area of the iris. A second step is to apply band-pass filtering to the unwrapped iris images. The convolution kernel was set to be the difference of 2-D Gaussian distributions with standard deviations equal to 3 and 12 pixels. A third step was the introduction of bi-directional alignment, when the blocks were selected and matched from the wavefront device to the laser and from the laser to the wavefront device. This essentially doubled the number of data points used for sinusoidal fitting.

Another difference in the matching was implemented as a special case for LASIK procedures. Instead of using LSE metric for block matching, a normalized correlation was used as a match criteria. This method was found to be more appropriate given different contrast levels of the wavefront image and the laser image of the eye with its flap lifted.

Experimental Torsional Tracking Results

Figure 18A:
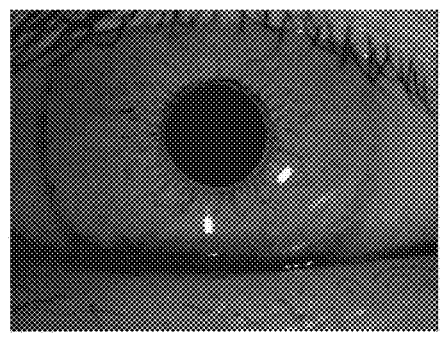
FIG. 18A is an original frame image of an eye.
Figure 18B:
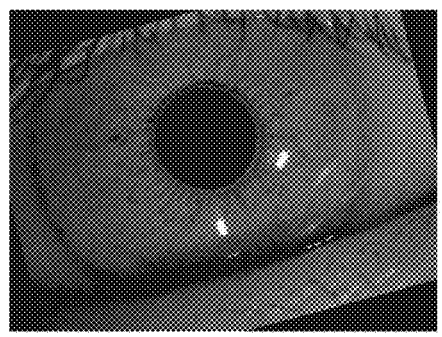
FIG. 18B is a final frame in which the image of the eye is rotated.

To test the torsional tracking algorithm, the algorithm was run through several tests. The first set of results using the methods and software of the present invention to track the torsional movement of the patient's eye involved artificial rotation of an image of a video frame from the laser surgical system's camera 20. The image was rotated by 1 degree counterclockwise for each subsequent frame. A total of 15 rotated frames were analyzed by the torsional tracking algorithm. The original frame and final frame are illustrated in FIGS. 18A and 18B, respectively. Application of the torsional tracking algorithm were accurate for every frame to a precision of within 0.2 degrees from its actual value.

Figure 19A:
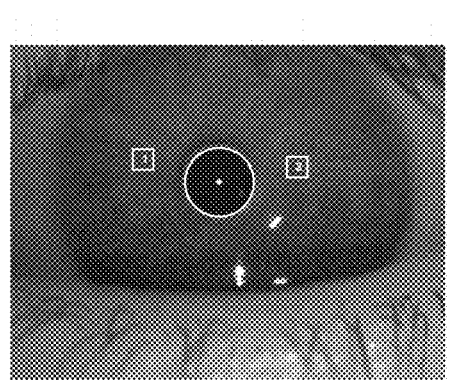
FIG. 19A is a reference frame.
Figure 19B:
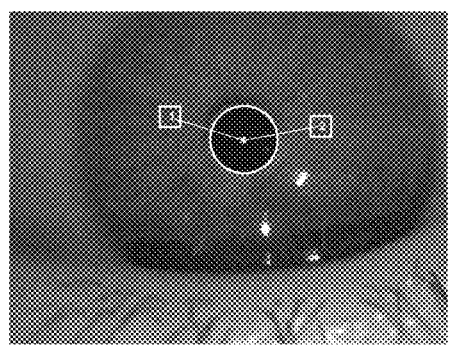
FIG. 19B is a zeroth frame having two pixel blocks marked for tracking.
Figure 20:
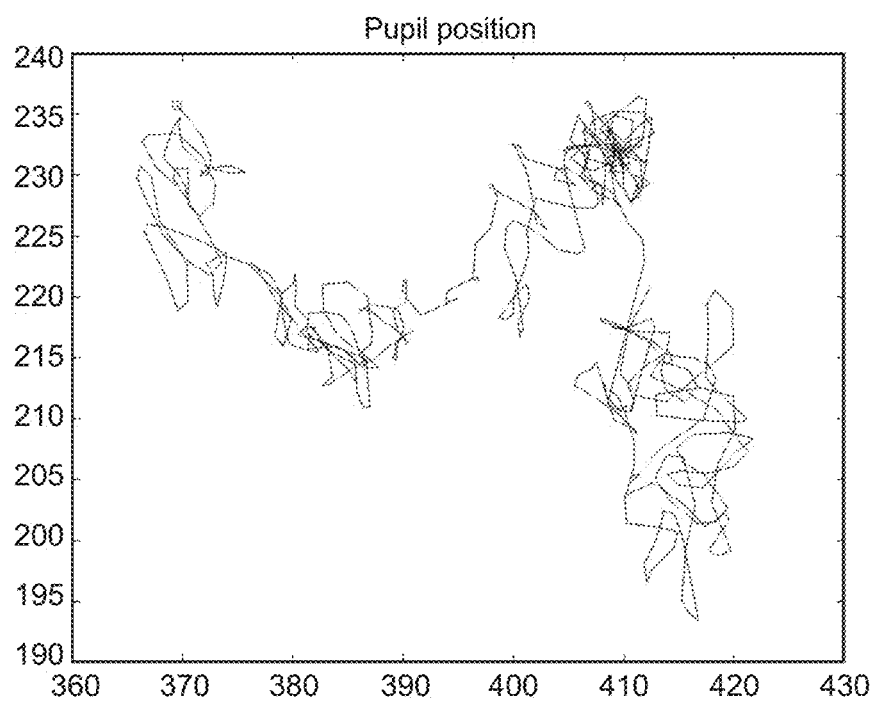
FIG. 20 is a chart of a pupil position over time.
Figure 21:
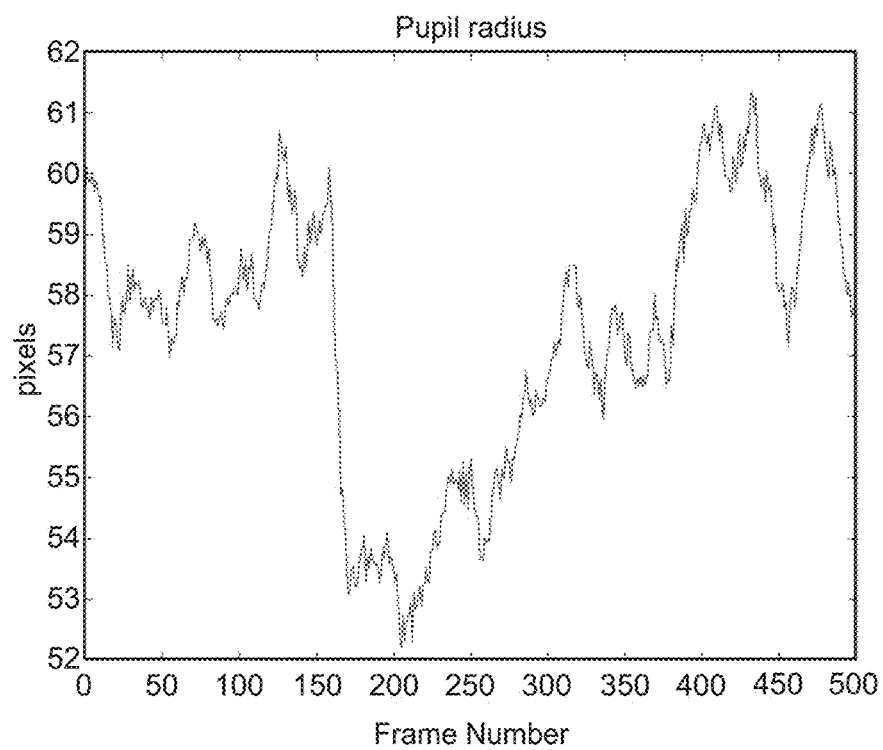
FIG. 21 is a chart of the pupil radius from frame 0 to frame 500.
Figure 22:
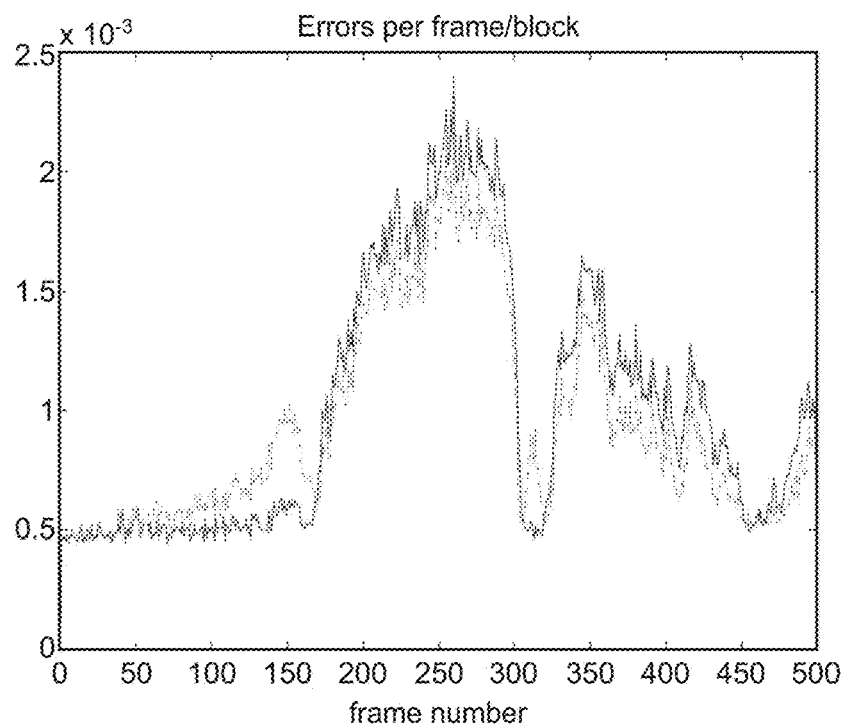
FIG. 22 is a chart that illustrates errors per frame/block.
Figure 23:
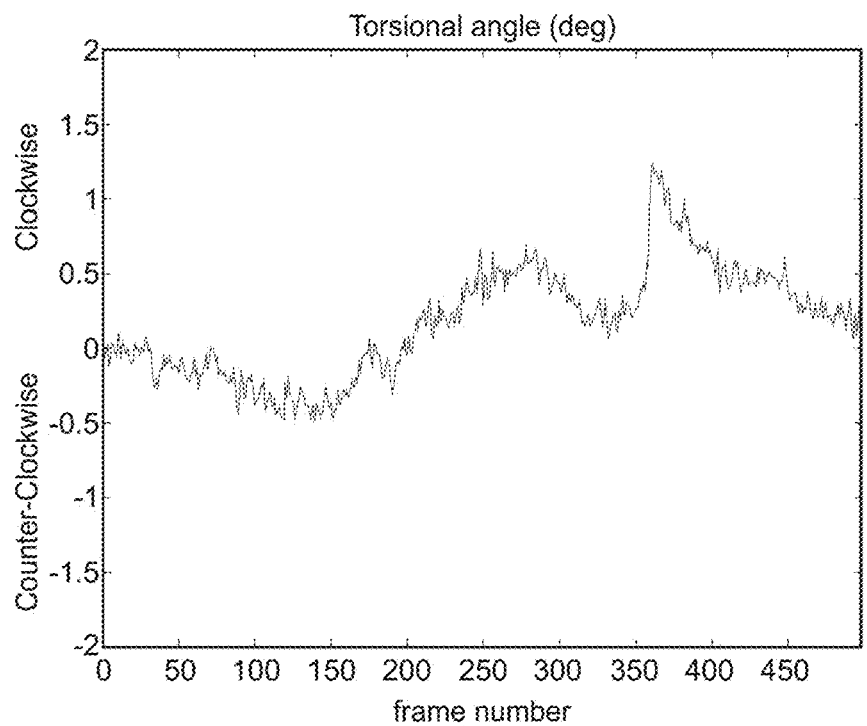
FIG. 23 is a chart that illustrates a measured torsional angle of the eye.

The second set of results comes from a 500-frame sequence capturing 25 seconds of real video of an eye. Several variables were tracked during the video processing: pupil center position, pupil radius, torsional angle, and error estimates for the two blocks tracked for each frame. The sequence was also visually inspected to verify the black match and the overall eye torsion. The zero$^{th}$ frame (FIG. 19A) was used as a reference with two 31×31 pixel blocks marked for tracking. The last frame shows the same blocks at the appropriate locations. (FIG. 19B). FIGS. 20-23 show the data extracted from the video sequence. FIG. 20 shows the pupil position over time. FIG. 21 shows the change of the pupil radius from frame 0 to 500. FIG. 22 illustrates errors per frame/block. FIG. 23 shows the torsional angle of the markers (relative to the first frame of the video).

Figure 24:
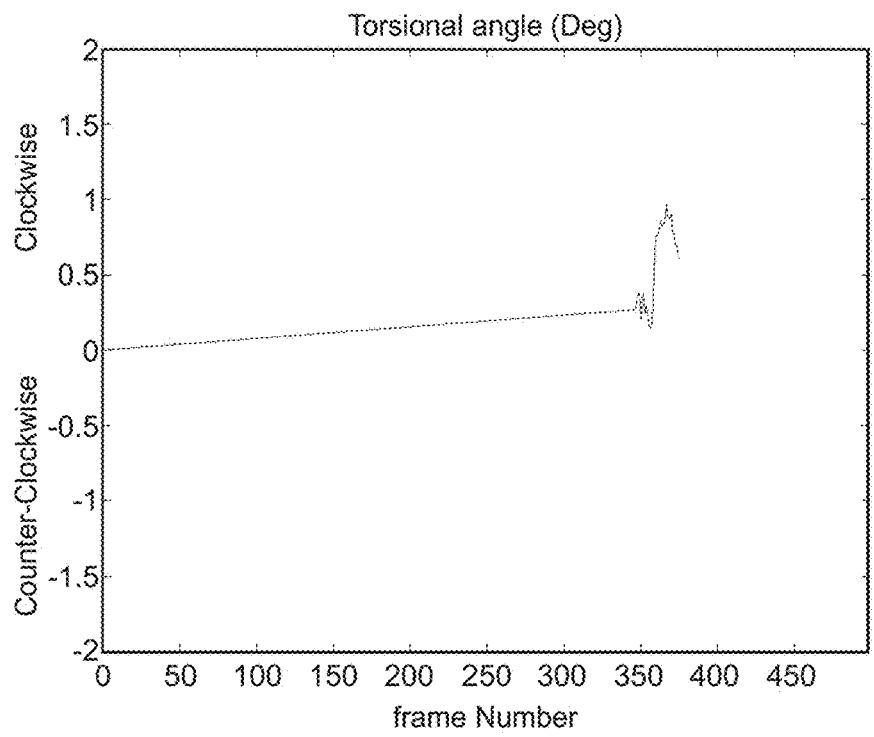
FIG. 24 depicts the tracking results for a 30-frame sequence starting with the $345^{th}$ frame.

The algorithm was tested to see the effect of the delay between the block selection and tracking initialization. This was accomplished by skipping the first 344 frames of the video sequence. FIG. 24 depicts the tracking results for the 30-frame sequence starting with the 345$^{th}$ frame. The data shows that the algorithm jumped to correct position and correctly tracked the blocks throughout the video sequence to within ¼ degree precision compared to the original torsional data. Skipping video frames is often required to give time to the torsional alignment algorithm to establish the rotational angle between the reference image and the second image (e.g., first frame of the video sequence).

Figure 25:
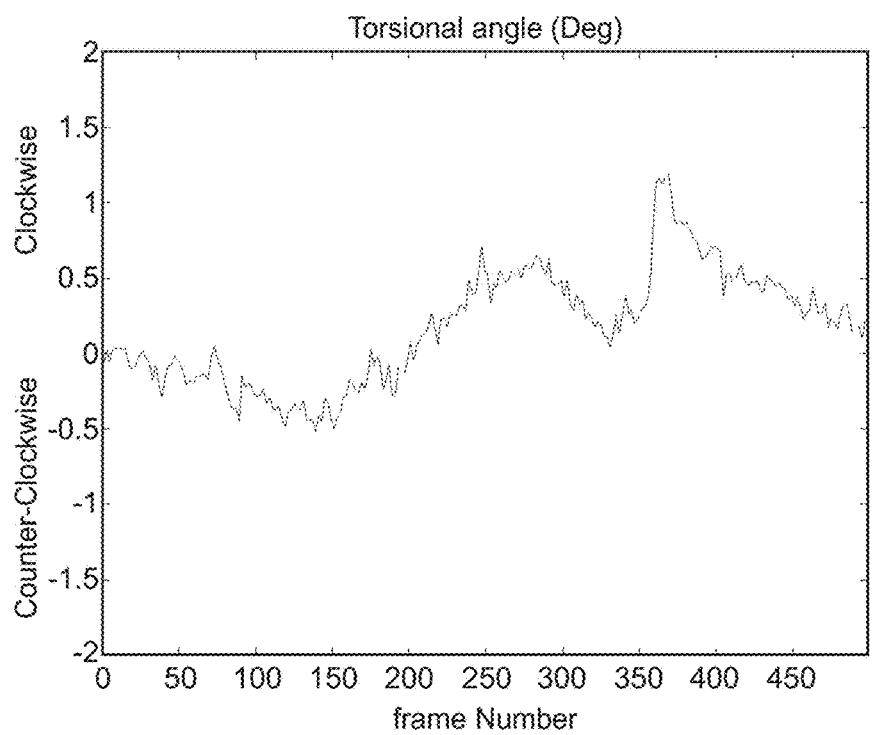
FIG. 25 is a chart that shows the torsional data extracted from the slower acquired sequence.

A third set of data was obtained by reducing the frame rate by a factor of two. FIG. 25 shows the torsional data extracted from the slower acquired sequence. Such data still matches the measurement extracted from the normal frame rate sequence illustrated in FIG. 23.

Figure 26A:
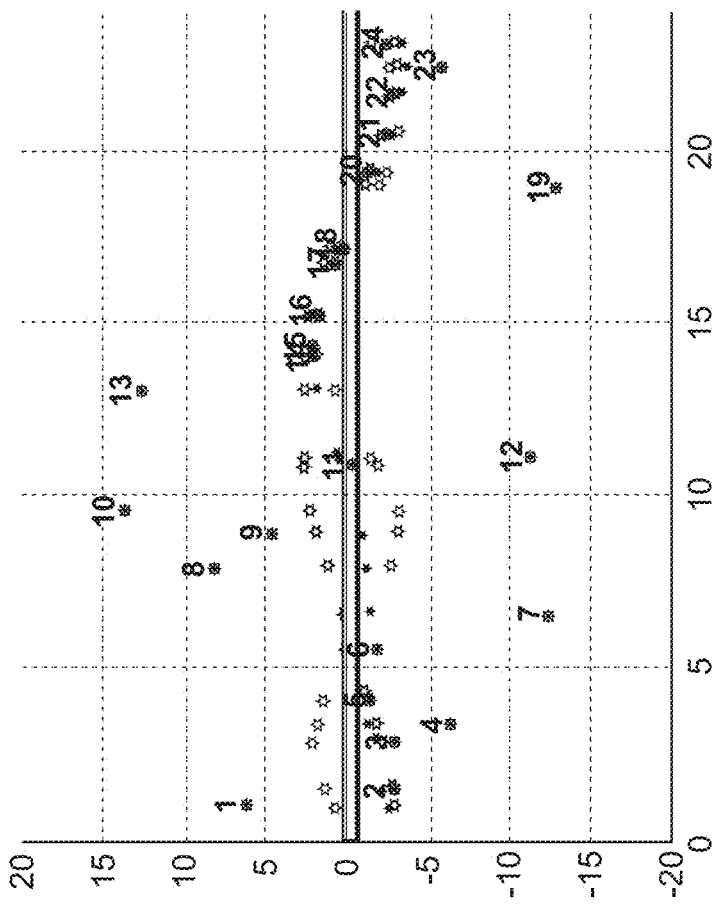
FIGS. 26A and 26B show alignment results using a sine-method between the wavefront measurement position of the iris and the first image of the video sequence.
Figure 26B:
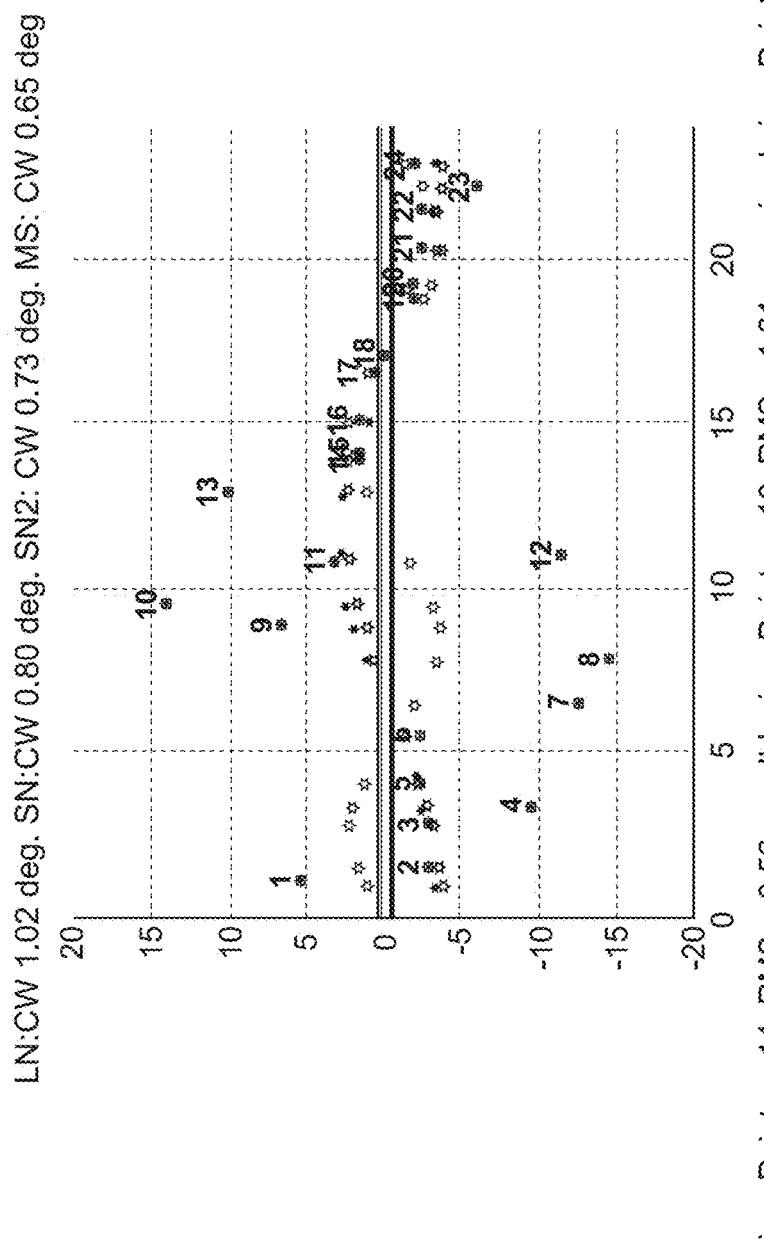

In order to test the accuracy of the torsional alignment (e.g., registration of the reference image with the first image of the video stream) and torsional tracking together, as well as the algorithm's ability to automatically select the blocks of texture in the reference image to track, the following test was performed. A video sequence of several hundred frames was captured under the laser with the torsional camera. Several seconds prior to the video sequence acquisition, a snapshot of the eye was taken through the laser camera. The iris image obtained from the wavefront measurement camera was aligned and registered with the snapshot image and the first frame of the video sequence. The alignment results using the "sine-method" between the wavefront measurement position of the iris and the first image of the video sequence was 0.04 degrees counterclockwise. (FIG. 26A). Alignment to the snapshot image was 0.80 degrees clockwise. (FIG. 26B).

The torsional tracking algorithm was engaged using the two images (snapshot and wavefront image) as a reference. The measurement of the torsional eye movements with respect to the reference image is depicted in FIGS. 27A and 27B. Estimated torsional angle reference to the first image of the video sequence (FIG. 27A) closely resembled the one referenced to the snapshot (FIG. 27B), with the exception of the constant offset of about 0.5 degrees counterclockwise. The total angle of rotation with respect to the wavefront image is computed as follows:

$$\theta_{total}(t)=\text{Tracking}[(\text{reference image,video})(t)+\text{Alignment}[\text{Wavefront reference image}]+=°$$

Figure 28:
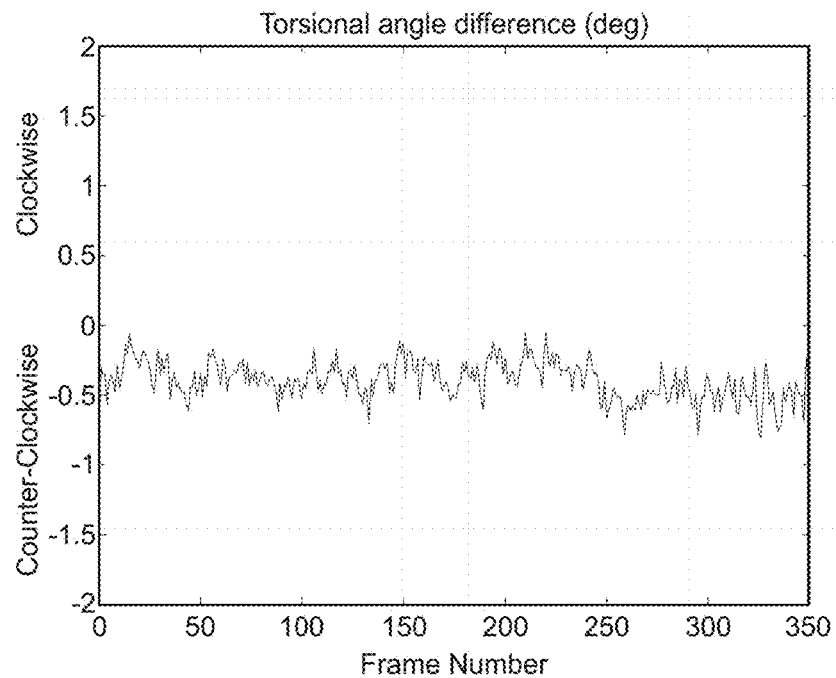
FIG. 28 shows a difference between two torsional angle estimates.

Therefore, for the above example, $\theta_{first\ video\ image}-0.04=\theta_{snapshot}+0.80$, where the alignment angle has a sign notation of clockwise being positive. The difference between the two estimates is shown in FIG. 28.

From the data, it can be estimated that the mean of the difference, $\mu=0.4$ degrees, and the standard deviation, $\sigma=0.12$ degrees. All of the error values for every video frame are less than one degree in magnitude. The mean shows the difference in the total alignment angle and its value is less than 1 degree, which is the specified tolerance for this one exemplary embodiment. It should be appreciated however, that other embodiments may have a tolerance that is more than 1 degree or less than 1 degree.

Figures 29A, 29B:
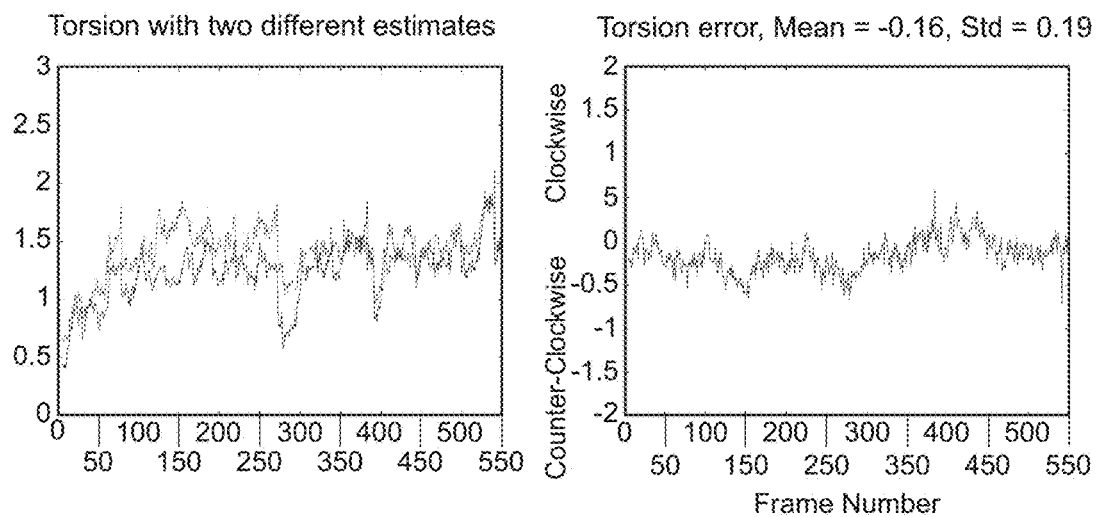
FIG. 29A illustrates two torsion estimates.
FIG. 29B illustrates the error between the two estimates of FIG. 29A.

The standard deviation shows that tracking different texture patches from different images has very small effect on the total torsional angle estimates. FIGS. 29A and 29B show two different torsional angle estimates that include the alignment with the wavefront measurement image. The reference frames for the two estimates were 0.41 degrees clockwise 134 (FIG. 29A) and 1.17 degrees clockwise 136 (FIG. 29A). The errors between the estimates are shown in FIG. 29B as a function of the frame number. As in previous tests, the errors do not exceed 1 degree for any frame.

It should be appreciated by a person of ordinary skill in the art that the above alignment and tracking algorithms are merely examples of some algorithms that can be used to align the images of the eyes and track the torsional rotation of the patient's eye, and other algorithms, using different methodologies can be used without departing from the spirit of the present invention.

While all the above is a complete description of the preferred embodiments of the inventions, various alternatives, modifications, and equivalents may be used. For example, while the above description has been described in the context of laser eye surgery, the above concepts may be useful in tracking the position and orientation of an eye for use in identification systems. Although the foregoing invention has been described in detail for purposes of clarity of understanding, it will be obvious that certain modifications may be practiced within the scope of the appended claims.

What is claimed is:

1. A laser eye surgery system for performing laser eye surgery on an eye of a patient, comprising:
    a laser assembly; and
    a computer system comprising a processor and computer executable code stored on a non-transitory computer readable medium, the computer executable code comprising instructions that when executed on the processor cause the processor to:
    receive a wavefront measurement of the eye;
    generate a laser treatment for the eye based on the wavefront measurement of the eye;
    receive a first image of the eye, wherein the first image of the eye is obtained during measurement of the wavefront measurement;
    receive a second image of the eye, wherein the second image of the eye is obtained when the eye of the patient is positioned in an optical axis of a laser beam of the laser assembly;
    align the second image of the eye with the first image of the eye by matching a plurality of discrete iris markers in the first image with corresponding iris markers in the second image to determine a pupil center and a torsional offset;
    center the laser treatment with the eye of the patient under the optical axis of the laser beam;
    determine, during delivery of the laser treatment by the laser assembly, a position and torsional orientation of the eye relative to the laser beam based on the pupil center and the torsional offset determined; and
    adjust delivery of the laser treatment by the laser assembly to compensate for changes of the position and torsional orientation of the eye.

2. The system of claim 1, wherein the computer executable code comprises instructions that when executed on the processor cause the processor to monitor the position and torsional orientation of the eye relative to the laser beam.

3. The system of claim 1, wherein the computer executable code comprises instructions that when executed on the processor cause the processor to track a position and orientation of a subset of the plurality of discrete iris markers in the first image relative to a common reference point.

4. The system of claim 3, wherein the common reference point is the pupil center.

5. The system of claim 3, wherein the common reference point is defined by a function of the pupil center and an iris center.

6. The system of claim 1, wherein the computer executable code comprises instructions that when executed on the processor cause the processor to locate at least one of an iris center and the pupil center in the first and second images.

7. The system of claim 1, wherein the first and second images of the eye comprise grayscale images of an iris of the eye.

8. The system of claim 1, wherein the plurality of discrete iris markers in the first image and the corresponding iris markers in the second image comprise high contrast markers.

9. The system of claim 1, wherein the computer executable code comprises instructions that when executed on the processor cause the processor to account for false matching of markers of the first and second images.

10. The system of claim 1, wherein the computer executable code comprises instructions that when executed on the processor cause the processor to scale a radial thickness of at least one of the first and second images.

11. A laser eye surgery system for performing laser eye surgery on an eye of a patient, comprising:
    a laser assembly; and
    a computer system comprising a processor and computer executable code stored on a non-transitory computer readable medium, the computer executable code comprising instructions that when executed on the processor cause the processor to:
    receive a wavefront measurement of the eye;
    generate a laser treatment for the eye based on the wavefront measurement of the eye;
    receive a first image of the eye, wherein the first image of the eye is obtained during measurement of the wavefront measurement;

receive a second image of the eye, wherein the second image of the eye is obtained when the eye of the patient is positioned in an optical axis of a laser beam of the laser assembly;

align the second image of the eye with the first image of the eye to determine a pupil center and a torsional offset, wherein the second image is aligned by dividing the second image of the eye into a circumference series of sectors, and by matching a plurality of markers in the first image, each of the plurality of markers being disposed in an associated sector so that the markers are circumferentially distributed, with corresponding markers in the second image;

center the laser treatment with the eye of the patient under the optical axis of the laser beam;

determine, during delivery of the laser treatment by the laser assembly, a position and torsional orientation of the eye relative to the laser beam based on the pupil center and the torsional offset determined; and adjust delivery of the laser treatment by the laser assembly to compensate for changes of the position and torsional orientation of the eye.

12. The system of claim 11, wherein the computer executable code comprises instructions that when executed on the processor cause the processor to monitor the position and torsional orientation of the eye relative to the laser beam.

13. The system of claim 11, wherein the computer executable code comprises instructions that when executed on the processor cause the processor to track a position and orientation of a subset of the plurality of markers in the first image relative to a common reference point.

14. The system of claim 13, wherein the common reference point is the pupil center.

15. The system of claim 13, wherein the common reference point is defined by a function of the pupil center and an iris center.

16. The system of claim 11, wherein the computer executable code comprises instructions that when executed on the processor cause the processor to locate at least one of an iris center and the pupil center in the first and second images.

17. The system of claim 11, wherein the first and second images of the eye comprise grayscale images of and iris of the eye.

18. The system of claim 11, wherein the plurality of markers in the first image and the corresponding iris markers in the second image comprise high contrast markers.

19. The system of claim 11, wherein the computer executable code comprises instructions that when executed on the processor cause the processor to account for false matching of markers of the first and second images.

20. The system of claim 11, wherein the computer executable code comprises instructions that when executed on the processor cause the processor to scale a radial thickness of at least one of the first and second images.

* * * * *